United States Patent
Hammerschmidt et al.

(10) Patent No.: US 11,090,583 B2
(45) Date of Patent: Aug. 17, 2021

(54) BOTTOM SECTION FOR BEING CONNECTED TO AN ASSEMBLY WITH PLATE SETTLER, AND ASSEMBLY WITH PLATE SETTLER

(71) Applicant: TAKEDA PHARMACEUTICAL COMPANY LIMITED, Osaka (JP)

(72) Inventors: Nikolaus Hammerschmidt, Vienna (AT); Alois Jungbauer, Vienna (AT); Hannah Engelmaier, Vienna (AT)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 16/444,300

(22) Filed: Jun. 18, 2019

(65) Prior Publication Data

US 2020/0016515 A1    Jan. 16, 2020

Related U.S. Application Data

(60) Provisional application No. 62/686,258, filed on Jun. 18, 2018.

(51) Int. Cl.
*B01D 21/24* (2006.01)
*B01D 21/00* (2006.01)
*C12N 5/071* (2010.01)

(52) U.S. Cl.
CPC ....... *B01D 21/245* (2013.01); *B01D 21/0006* (2013.01); *B01D 21/0045* (2013.01);
(Continued)

(58) Field of Classification Search
CPC ............ B01D 21/0039; B01D 21/0042; B01D 21/0045; B01D 21/0087; B01D 21/2405; B01D 21/245
(Continued)

(56) References Cited

U.S. PATENT DOCUMENTS 2,793,186 A    5/1957 Dunell et al.
2,883,059 A    4/1959 Puddington et al.
(Continued)

FOREIGN PATENT DOCUMENTS

GB     753646    7/1956
GB    2011877  * 7/1979
(Continued)

OTHER PUBLICATIONS

International Search Report and Written Opinion dated Sep. 30, 2019 in connection with PCT/EP2019/066009.

*Primary Examiner* — Christopher Upton
(74) *Attorney, Agent, or Firm* — Troutman Pepper Hamilton Sanders LLP

(57) ABSTRACT

This disclosure relates to a bottom section for being connected to an assembly for separating a solid component from a fluid. The assembly includes an inclined plate settler with at least one sedimentation channel for letting a solid component to be separated settle, said plate settler comprising a lower portion and an upper portion, wherein said at least one sedimentation channel extends from the lower portion to the upper portion. The bottom section is configured to be connected to the lower portion of the inclined plate settler. The bottom section comprises at least one inlet channel for feeding a fluid comprising the solid component to be separated to the plate settler, and at least one collection channel for collecting a settled solid component descending from the at least one sedimentation channel. Said at least one inlet channel and said at least one collection channel are fluidly separated from each other, said inlet channel and said collection channel being connectable to said at least one sedimentation channel, to form fluid connections between said at least one inlet channel and said at least one sedimentation channel and between said at least one collection (Continued)

channel and said at least one sedimentation channel, respectively.

36 Claims, 13 Drawing Sheets

(52) U.S. Cl.
CPC ..... *B01D 21/0087* (2013.01); *B01D 21/2405* (2013.01); *C12N 5/0682* (2013.01)

(58) Field of Classification Search
USPC ............ 210/802, 803, 519, 521, 522, 532.1
See application file for complete search history.

(56) References Cited

U.S. PATENT DOCUMENTS

| | | | |
|---|---|---|---|
| 3,240,336 A | 3/1966 | Condolios | |
| 3,494,475 A * | 2/1970 | Hedstrom | B01D 21/0045 210/521 |
| 3,552,554 A * | 1/1971 | Olgard | B01D 21/2416 210/519 |
| 3,687,298 A * | 8/1972 | Rozkydalek | B01D 21/245 210/519 |
| 3,706,384 A * | 12/1972 | Weijman-Hane | B01D 21/2405 210/519 |
| 3,886,064 A * | 5/1975 | Kosonen | B01D 21/2405 210/519 |
| 2002/0074265 A1 | 6/2002 | Gomez | |
| 2004/0251218 A1* | 12/2004 | Giordani | B01D 21/0045 210/800 |
| 2012/0312741 A1 | 12/2012 | Pahsaian et al. | |

FOREIGN PATENT DOCUMENTS

| | | |
|---|---|---|
| GB | 2011877 A | 7/1979 |
| SU | 946591 A1 | 7/1982 |

* cited by examiner

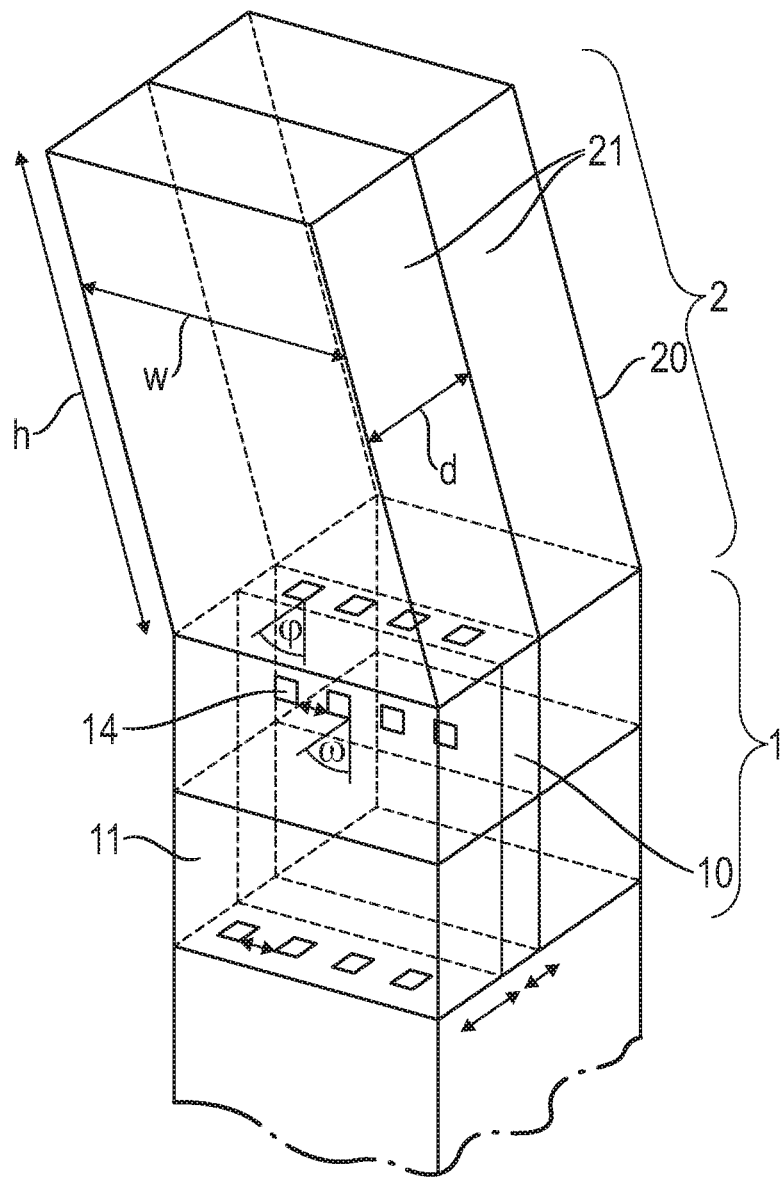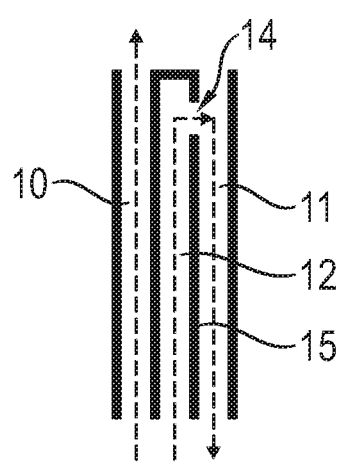
Fig. 3
Fig. 4

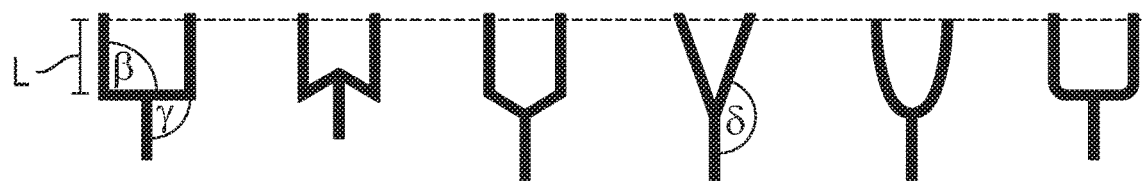
Fig. 9A  Fig. 9C  Fig. 9E
   Fig. 9B  Fig. 9D  Fig. 9F
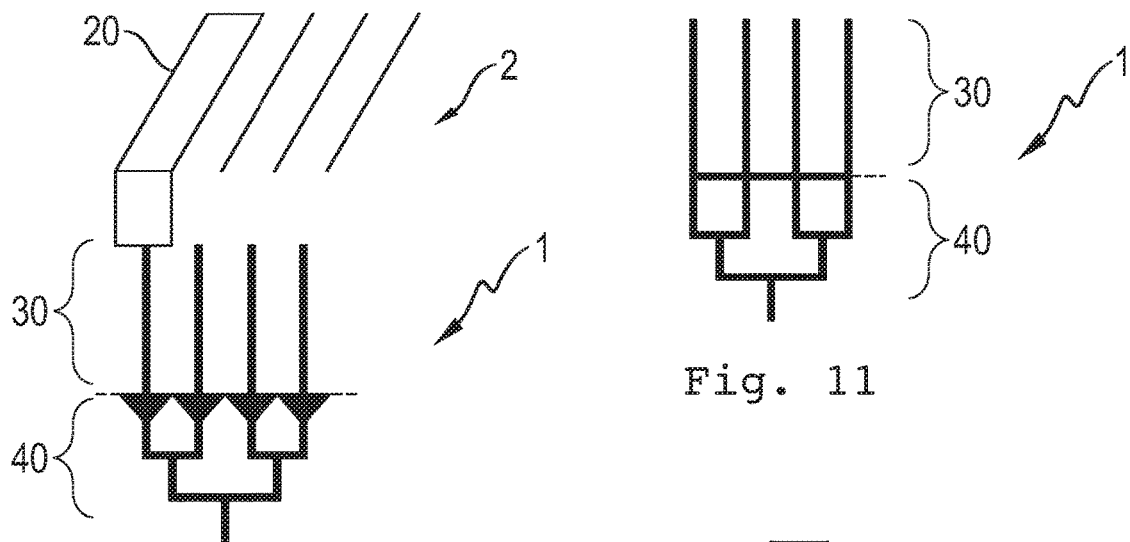
Fig. 10
Fig. 11
Fig. 12
Fig. 13

BOTTOM SECTION FOR BEING CONNECTED TO AN ASSEMBLY WITH PLATE SETTLER, AND ASSEMBLY WITH PLATE SETTLER

CROSS-REFERENCE TO RELATED APPLICATION

This application claims priority from U.S. Provisional Application No. 62/686,258, filed Jun. 18, 2018, which is hereby incorporated by reference in its entirety.

TECHNICAL FIELD

The present disclosure relates to a bottom section for being connected to an assembly for separating a solid component from a fluid, said assembly including an inclined plate settler. The disclosure also relates to an assembly comprising such a bottom section and an inclined plate settler. The disclosure further relates to the use of a bottom section for being connected to an assembly comprising an inclined plate settler. The disclosure also relates to a method for separating solid components from a fluid.

TECHNICAL BACKGROUND

Assemblies for performing a separation of a component from a fluid may comprise an inclined plate settler. The sedimentation plates, on which the component to be separated can settle, of an inclined plate settler extend in an oblique rather than in the vertical direction, i.e., in a direction that is slanted with respect to the direction of gravity. Examples of inclined plate settlers are disclosed in US 2012/0302741 A1, U.S. Pat. No. 2,793,186 A1, GB Pat. No. 753,646 A1, and US 2002/0074265 A1.

A fluid is supplied to such a plate settler at its bottom end with a sufficiently high pressure such that the fluid flows upwards along the settler's sedimentation plates. The solid component to be separated may, e.g., already be present in the supplied fluid in solid form. Alternatively, the component to be separated may, e.g., precipitate under the influence of gravity. The remainder of the fluid flows on and is eventually exhausted from an outlet at the top end of the plate settler. The separated component (e.g., a solid component) is collected from the bottom end of the plate settler.

The bottom end of the plate settler may be connected to a component, often referred to as a "bottom section", comprising supply channels for supplying a fluid containing the component to be separated and collection channels for collecting the separated component.

An inclined plate settler may comprise several sedimentation plates. A separation process can thus simultaneously take place at each of the sedimentation plates. Because both fluid comprising the component to be separated is supplied and the separated component is collected at the bottom end of the plate settler, the separated component may get mixed into the newly supplied fluid and thus be carried back upwards along the plate settler. This may lower the efficiency of the separation process. It would thus be desirable to further increase the efficiency of a separation process in a plate settler.

There is, hence, a need for an assembly including an inclined plate settler and/or for a bottom section for such an assembly suited to address at least one of the above-mentioned shortcomings.

SUMMARY

Aspects of the above-mentioned object are achieved by embodiments of a bottom section, by embodiments of an assembly in accordance with the present disclosure, and by the use of a bottom section in accordance with the present disclosure, respectively.

Aspects of the present disclosure relate to a bottom section for being connected to an assembly for separating a solid component from a fluid, said assembly including an inclined plate settler with at least one sedimentation channel for letting a solid component to be separated settle, the plate settler comprising a lower portion and an upper portion, and the at least one sedimentation channel extending from the lower portion to the upper portion, wherein the bottom section is configured to be connected to the lower portion of the inclined plate settler.

The term "bottom section" is in this context not to be understood to imply that the bottom section necessarily is to be positioned at the "bottom" of an assembly in use and/or that the assembly rests on the bottom section (such that it would play the role of a "foot part"). The bottom section may or may not be at the bottom. In other words, the bottom section itself may, e.g., rest on another component positioned partially or fully below the bottom section. The bottom section may or may not constitute a foot member on which the assembly partially or fully rests, depending on the embodiment(s) in question.

The disclosure encompasses separately formed bottom sections that are (directly or indirectly) connectable to an inclined plate settler. The disclosure however also encompasses assemblies with bottom sections that are a part of a larger, integrally formed part (e.g., the bottom section may be made as one piece together with another component of an assembly).

The bottom section may comprise at least one inlet channel for feeding a fluid comprising the solid component to be separated to the plate settler, and at least one collection channel for collecting a settled solid component descending from the at least one sedimentation channel. The solid component may be collected as such or it may be collected in a suspended form, forming part of fluid. The solid component may already be present in solid form in the supplied fluid, or it may precipitate from the fluid in the plate settler. The collection channel may also be used to collect a fluid component (e.g., a heavier component) of a fluid supplied to an assembly comprising a plate settler.

Said at least one inlet channel and said at least one collection channel are fluidly separated from each other. By being "fluidly separated" it is meant that there is no direct fluid connection between the inlet channel and the collection channel in the bottom section. For example, a wall in the bottom section may separate the inlet channel and the collection channel. However, an indirect fluid connection (e.g., via a sedimentation channel in an assembly connected to the bottom section) may of course be present. The latter is not excluded by the absence of "being fluidly separated", in accordance with the terminology used in this context.

The inlet channel and the collection channel may be connectable to the at least one sedimentation channel of an assembly to which the bottom section is connectable, to form fluid connections between said at least one inlet channel and said at least one sedimentation channel and between said at least one collection channel and said at least one sedimentation channel, respectively.

The fluid separation between inlet channel and collection channel (i.e., the absence of a direct fluid communication) may promote a better control over the behavior of fluid flows in the bottom section. Specifically, turbulences arising from mixtures of fluid being supplied and the descending separated solid component (e.g., a precipitate) and/or a descending separated fluid (e.g., comprising a solid component to be separated) in the bottom section or by virtue of the bottom section may be lowered or even avoided. Also, less or no separated component may be mixed into newly supplied fluid. Thus, the efficiency of the separation process carried out with an assembly connected to the bottom section may be increased by the bottom section in accordance with these embodiments.

According to some embodiments, the bottom section is configured to be connected to an assembly with a plate settler comprising a plurality of sedimentation channels and separation plates separating neighboring sedimentation channels. The bottom section may comprise a plurality of inlet channels and a plurality of collection channels, wherein said at least one inlet channel and said at least one collection channel are fluidly separated from all remaining inlet and collection channels, respectively.

The number of inlet channels may be equal to or different from the number of collection channels. Likewise, the respective numbers of inlet channels and of collection channels may be equal to or differ from the number of sedimentation channels of an assembly, to which the bottom section is configured to be connected. For some embodiments, the number of inlet channels is identical to the number of collection channels and is also identical to the number of sedimentation channels so that the bottom section comprises one inlet channel and one collection channel per sedimentation channel. This may particularly increase the efficiency of the separation process of an assembly connected to the bottom section.

The flow connection between said at least one inlet channel and the corresponding sedimentation channel and said at least one collection channel and the corresponding sedimentation channel may be separate from fluid connections between all other sedimentation channels and all other inlet channels and collection channels, respectively. This way, turbulent flows and/or other flow disturbances in the bottom section associated with the pair of channels comprising said at least one inlet channel and said at least one collection channel and the corresponding sedimentation channel and other channel pairs may be lowered or even fully avoided. This may further increase the efficiency of an assembly connected to the bottom section.

The bottom section in accordance with some embodiments may comprise one individual inlet channel and one individual collection channel for at least 50% of the sedimentation channels of a corresponding assembly, to which the bottom section is configured to be connectable. This may increase the efficiency as the degree of pairing is high in the sense that the number of channels not associated with a corresponding paired channel is 50% or lower. This may allow to lower or to suppress associated turbulent flows or other flow disturbances associated with neighboring channels that are not separated in terms of belonging to different channel pairs.

Optionally, there may be provided one individual inlet channel and one individual collection channel for at least 75% of the sedimentation channels of a corresponding assembly, or for at least 95% of the sedimentation channels. This may further increase the efficiency, respectively.

In accordance with some embodiments, the bottom section may comprise one individual collection channel and one individual inlet channel for each of the plurality of sedimentation channels, wherein a separate fluid connection is formable for each corresponding pair of inlet channel and sedimentation channel and for each corresponding pair of collection channel and sedimentation channel, respectively. This may lead to a particularly high efficiency of the assembly comprising the plate settler combined with the bottom section. Specifically, disturbance flows associated with neighboring pairs of channels may be minimized and losses of a separated solid component may be kept low or even avoided.

According to some embodiments, the bottom section may be configured to be connected to an assembly oriented in a use position such that end portions of the inlet channels and end portions of the collection channels proximate to the plate settler extend in the direction of gravity. In other words, a connection portion of the bottom section to be connected to an assembly may be oriented with respect to the end portions of the inlet channels and collection channels, respectively, such that when the connection portion is oriented with respect to the direction of gravity in the state of connection between assembly and bottom section ready for use, the end portions extend in the direction of gravity. According to some embodiments there may be an angle between the extension direction, when the bottom section is oriented as described, and the direction of gravity. The angle may lie in a range of 0° to 15°, optionally between 0° and 10°, or even between 0° and 5°. This may further increase efficiency.

An extension direction identical or similar to the direction of gravity (i.e., a vertical direction) of the end portions may promote similar or even equal hydrostatic pressures in different supply channels and/or collection channels, respectively. This means that a homogeneous use of an apparatus with a plate settler connected to the bottom section may be promoted.

Bottom sections in accordance with some embodiments may comprise at least one wash fluid supply channel for supplying a wash fluid (or a different fluid) to a sedimentation channel or to a collection channel, said at least one wash fluid supply channel being fluidly separated from other wash fluid supply channels and from all inlet channels. Again, the fluid separation refers to no direct communication within the bottom section but does not exclude the possible presence of an indirect connection (e.g., via a sedimentation channel). Being fluidly separated from other wash fluid supply channels and from the inlet channels may lower or even avoid the occurrence of efficiency lowering flow disturbances such as, e.g., turbulences associated with neighboring channels.

One or several wash fluid supply channels provide the possibility to supply another fluid, for example, a wash fluid that may be used to promote the collection of a separated fluid or solid component (e.g., a precipitate). This may promote the efficiency of a separation process. For example, when a solid component tends not to be drained efficiently, possibly because there is a tendency to adhere to parts of a sedimentation plate or, another part of an assembly, or, e.g., to a collection channel, supplying a wash fluid may play an efficient contribution to collect the solid component and to "wash" it down through one or several collection channels of the bottom section. A wash fluid may also promote the separation of a solid component and the (remainder of) a supplied fluid. This may be of importance, for example, because the fluid phase may be of high value and/or as it may contain impurities, which one wants to get rid of. The use of a wash fluid is optional in the sense that removing bound or adhering solids may also be accomplished without the application of a wash fluid.

The at least one wash fluid supply channel and the at least one collection channel corresponding to the same sedimentation channel may be fluidly connected, for example, by an opening in a wall portion shared by said wash fluid supply channel and said collection channel. The fluid connection may be direct in the sense that the fluid connection may exist within the bottom section. This may inhibit or even prevent a supplied wash fluid accidentally being guided along the sedimentation channel and being drained out of the top end. It may also lower the amount of wash fluid being transported upward along the plate settler and being drained at the top end.

The fluid connection between fluid supply channel and collection channel in the bottom section may increase the efficiency of a process of washing out a separated fluid or solid component and to collect it via the collection channel(s). It may also additionally increase the flow efficiency by inhibiting or preventing flow disturbances, because a wash fluid may directly be guided towards (a) collection channel(s).

The bottom section in accordance with some embodiments may comprise at least one intrachannel distributing portion for evenly distributing a fluid flow through a part of a first channel proximate to a corresponding sedimentation channel over at least one direction of extension across the cross-section of said particular channel. The first channel may be directly adjacent to the sedimentation channel to be connected to it, or there may be a further component in-between. The intrachannel distributing portion may increase the efficiency of the use of an apparatus with a plate settler because it may, e.g., increase the homogeneity of the load applied to the associated sedimentation channel in question.

Said first channel is an inlet channel or a collection channel or a wash fluid supply channel. An intrachannel distributing portion may, more generally, be provided to one or several inlet channels and/or one or several collection channels and/or one or several wash fluid supply channels. For some embodiments, there is one intrachannel distributing portion for each inlet channel, one intrachannel distributing portion for each collection channel, and one intrachannel distributing portion for each wash fluid supply channel present. This may increase the efficiency of the bottom section in particular, as it may promote a particularly even flow distribution over all of the mentioned channels of the bottom section, both for fluids supplied to a connected assembly as well as for fluids/components drained (collected) therefrom.

The bottom section in accordance with some embodiments may comprise at least one interchannel distributing portion for evenly distributing a fluid flow in the direction to or the direction from a plate settler over a plurality of inlet channels and/or wash fluid supply channels and/or collection channels. There may be one or several interchannel distributing portions. One or several interchannel distributing portions may be provided for a part of or all of the inlet channels, one or several interchannel distributing portions may be provided for a part of or all of the collection channels, and one or several interchannel distributing portions may be provided for a part of or all of the wash fluid supply channels. However, several interchannel distributing portions may in this context also simply just be referred to as "an interchannel distributing portion".

According to some embodiments, all inlet channels, all collection channels, and all wash fluid supply channels may be fluidly collected to an interchannel distributing portion. This may increase the efficiency of the bottom section in particular, as it may promote a particularly even flow distribution over all of the present channels, both for fluids supplied to a connected assembly as well as for fluids drained therefrom. According to some embodiments, a first interchannel distributing portion may be connected to all inlet channels, a second interchannel distributing portion may be connected to all collection channels, and a third interchannel distributing portion may be connected to all wash fluid supply channels. The terms "first", "second", and, "third" are just used as labels to distinguish between the three interchannel distributing portions.

The intrachannel distributing portion may connect an upper part of the first channel with a lower part of said first channel, wherein said upper part is located proximate to the corresponding sedimentation channel. The latter means that the upper part is closer to where the bottom section is to be connected to an apparatus including a plate settler than the lower part.

The lower part of the first channel may be split into two (or more) connecting channels of equal first cross-sections, and said connecting channels are optionally at least once further split into (two or more) respective connecting sub-channels with respective equal second cross-sections. With "equal first cross-sections" and "equal second cross-sections", it is meant that all the cross-sections of the channels after the first split are equal, and likewise for the channels after the second split. Channels after a split may or may not have the same cross-sections as the channels before the split. The first cross-sections may thus be identical to or different from the respective second cross-sections, etc.

End portions of all of the connecting sub-channels after the respective last splits are connected to the upper part so as to be evenly distributed over a distributing direction. This may particularly promote the evenness of the distribution of fluid effected by the intrachannel distribution portion. The flow speed may or may not be kept substantially constant before and after a bifurcation (a point where a channel is split into two or more channels). According to some embodiments, all splits may double the number of channels. For other embodiments, split into three or more channels may be effected at a split point. Also different splitting numbers may be associated with different split points.

Subsequent splits may be effected at the same height when the channels are oriented to extend in a vertical direction. For example, the first split may be into two channels, and after the Nth set of splits (wherein each set is at a particular height), there may be 2N channels. The height differences between subsequent sets of splits may be identical or may be different. The cross-sections of all the channels may be identical. The cross-sections may be the same or different between each pair of channels corresponding to different stages in the bifurcated channel system with respect to the number of preceding sets of splits.

Each of the one or several interchannel distributing portions may comprise an upper portion to be connected to one or several inlet channels or one or several wash fluid channels or one or several collection channels, and a lower portion. The lower part may be split into two connection channels of equal first cross-section. Said connection channels may at least once further split into respective connection sub-channels of respective other equal cross-sections, wherein the first cross-sections are identical to or different from the respective other cross-sections, and wherein end portions of all of the connection sub-channels after the respective last splits are connected to the upper portion so as to be evenly distributed over a distributing direction. The distributing direction may be substantially or completely perpendicular to the extension direction of at least a part of the inlet channels and/or collection channels, and/or wash fluid supply channels.

This may particularly promote the evenness of the distribution of fluid effected by the interchannel distribution portion. The flow speed may or may not be kept substantially constant before and after a bifurcation (a point where a channel is split into two or more connection channels). According to some embodiments, all splits may double the number of channels. For other embodiments, splits into three or more channels may be effected at a split point. The number of splits at a split point may differ between split points or be the same for all of them.

Subsequent splits may be effected at the same height when the connection channels are oriented to extend in a vertical direction. For example, the first split may be into two connection channels, and after the Nth set of splits (wherein each set is at a particular height), there may be 2N channels. The height differences between subsequent sets of splits may be identical or may be different. The cross-sections of all the connection channels may be identical. The cross-sections may be the same or different between each pair of connection channels corresponding to different stages in the bifurcated channel system with respect to the number of preceding sets of splits.

According to some embodiments, the intrachannel distributing portion and the interchannel distributing portion may be connected. Serially combining the two types of distributing portions may particularly promote the evenness of flow distribution and thus be particularly beneficial to the efficiency of the bottom section (and thus of an apparatus connected to the bottom section). The intrachannel distributing portion may be configured to be arranged more proximately to the plate settler than the interchannel distributing portion.

There may be one interchannel distributing portion connected to several intrachannel distributing portions, one of the latter being connected to each inlet channel, and/or there may be one interchannel distributing portion connected to several intrachannel distributing portions, one of the latter being connected to each collection channel. There may be one interchannel distributing portion connected to several intrachannel distributing portions, one of the latter being connected to each wash fluid supply channel. When there is one intrachannel distributing portion for each inlet channel, one for each collection channel, and one for each wash fluid supply channel, respectively, and when the respective sets of inlet channel-associated intrachannel distributing portions, collection channel-associated intrachannel distributing portions, and wash fluid channel-associated intrachannel distributing portions each are preceded (in terms of the flow direction towards a connected apparatus) by one or several interchannel flow distributing portions, this may particularly promote the effectiveness and efficiency of the bottom section.

In particular, it may particularly promote the evenness of the flow distribution towards an apparatus and thus also of flows in various sedimentation channels of an inclined plate settler.

All of the inlet channels and the collection channels may be provided in pairs in the sense that there may always be a collection channel for every inlet channel (and vice versa) such that one pair is associated with one or several corresponding sedimentation channels of a plate settler, respectively. All of the inlet channels, collection channels, and wash fluid supply channels may be provided as triplets.

All of the inlet channels may be fueled by one corresponding interchannel distributing portion each, all of the collection channels may be joined by one corresponding interchannel distributing portion. All wash fluid supply channels may be fueled by a respective corresponding interchannel distributing portion.

All of the inlet channels may be associated with one intrachannel distributing portion, all of the collection channels may be associated with one intrachannel distributing portion. All of the wash fluid supply channels may be associated with one intrachannel distributing portion. The association is to be understood to express that one respective intrachannel distributing portion is provided in the fluid flow path leading towards the corresponding inlet channel.

For some embodiments of the bottom section that comprise one or several intrachannel distributing portions and one or several interchannel distributing portions, a distributing direction of the intrachannel distributing portions may be a longitudinal extension direction of a cross-section of a connecting end part of the first channel to be located proximate to the plate settler. The first channel may also entirely extend in this mentioned direction. The distributing direction of the interchannel distributing portions may be perpendicular to the distributing direction of the intrachannel distributing portions. This may lead to a particularly efficient flow distribution pattern. In particular, it may allow for a compact build of the bottom section.

The one or several intrachannel distributing portion(s) may be fractal flow distributors. Likewise, the one or several interchannel distributing portion(s) may be fractal flow distributors. The fractal flow distributors split subsequently in several split levels and can be scaled up or down by increasing or decreasing the number of split levels.

Some embodiments of the bottom section are configured to be connected to an assembly that has bottom surfaces of neighboring sedimentation channels extending parallel to one another, said bottom surfaces including at least a part that is not inclined in any direction other than the direction of inclination of the sedimentation channels. Also the entire bottom surfaces may be inclined only in the direction of inclination of the sedimentation channels.

The angle of inclination of the sedimentation channels with respect to the direction of gravity may lie in a range of 5° to 85° (or 15° to 75°). This may promote (or even further promote) the efficiency of a separation process. According to some embodiments, the angle lies in a range of 50° to 70°, optionally in a range of 55° to 65°, and optionally in a range of 58° to 62°. An angle within these increasingly narrower ranges may increasingly further promote the efficiency of a separation process.

Another aspect of this disclosure relates to an assembly for separating a solid component from a fluid. The assembly may comprise an inclined plate settler with a lower portion, an upper portion, and at least one sedimentation channel for letting a solid component to be separated settle. The sedimentation channel may extend from the lower portion to the upper portion.

The plate settler may be an inclined plate settler. It may be configured to be oriented during use such that the at least one sedimentation channel extends from the lower portion to the upper portion in a direction that is inclined with respect to the direction of gravity. The at least one sedimentation channel of the plate settler may be connected to a fluid outlet for draining a rest fluid at the upper portion and connected to a bottom section according to any one of the previously embodiments at the lower portion. Rest fluid, from which a fluid (or only a solid component) to be separated has been partially or fully separated, may be drained from the upper portion through the fluid outlet.

The assembly may comprise a plurality of sedimentation channels for letting a solid component to be separated settle, said sedimentation channels extending from the lower portion to the upper portion, and the plate settler may further comprise separation plates separating neighboring channels. The plate settler may be configured to be oriented during use such that the separation plates do not overlap in the direction of gravity. The separation plates may be oriented in the direction of gravity in the sense that they are vertically extending separation walls between neighboring sedimentation channels, when the assembly is installed such that it is oriented for use.

The plurality of sedimentation channels may be connected to at least one fluid outlet for draining a rest fluid at the upper portion. The plurality of sedimentation channels is connected to a bottom section according to any one of the previous claims at the lower portion. Each sedimentation channel of said plurality may be connected to one or several inlet channel(s) and one or several collection channel(s), and it may further also be connected to one or several wash fluid supply channel(s). According to some embodiments, a one-to-one correspondence between pairs of inlet and collection channels and one sedimentation channel may be realized, and according to some embodiment there may be one triplet, consisting of one inlet channel, one collection channel and one wash fluid supply channel, for one sedimentation channel.

The width of sedimentation channels may generally for embodiments of the assembly in accordance with the present disclosure lie in a range of 5 cm to 200 cm, optionally a range of 40 cm to 150 cm. The height of settling plates (the bottoms of the sedimentation channels) may generally lie in a range of 10 cm to 200 cm. The distance between two settling plates may generally lie in a range of 0.3 cm to 10 cm.

The number of fluid outlets per cm plate width (after a last split of a flow distributor located closest to the plate settler) may lie in a range of 0.2 outlets/cm to 2 outlets/cm, optionally in a range of 0.5 outlets/cm to 1 outlet/cm.

The cross-section in longitudinal direction of fluid channels of the flow distributors of a bottom section in accordance with the present disclosure may be (at least partially) square shaped or of rectangular shape or circular shape.

This disclosure also relates to the use of a bottom section according to any one of the embodiments described herein with an assembly according to any one of the embodiments described herein (in so far not incompatible), such that a relative difference between hydrostatic pressures in different sedimentation channels does not exceed a threshold of 10%. Optionally, the difference does not exceed a threshold of 5%, and optionally it does not exceed a threshold of 3%. These thresholds may (to an increasing degree with a lower threshold value) ensure very similar (or even substantially or fully identical) hydrostatic pressures in different sedimentation channels. This promotes a homogeneous and equilibrated use of the assembly and thus a higher efficiency, because it may make optimal use of the assembly's capacity.

According to some embodiments of the use of an assembly, said use comprises supplying a fluid comprising a solid component to be separated to the plate settler through the at least one inlet channel, and a wash buffer fluid through the at least one wash fluid supply channel, wherein a density of the wash buffer fluid is equal to or higher than a density of the fluid comprising the solid component to be separated. This may increase the efficiency of the desired separation process. It may also lower or even avoid losses of wash fluid as the tendency of wash fluid accidentally being transported up the sedimentation channel (and possibly even being drained through a top end outlet) may be lowered.

The disclosure also relates to a method for separating solid components from a fluid. Said method comprises a step of feeding fluid comprising the solid components to the at least one inlet channel of the bottom section in accordance with the present disclosure; a step of letting the solid components settle; a step of draining (i.e., collecting) the rest fluid (i.e., the solid-depleted fluid); and a step of collecting the settled components through the at least one collection channel of said bottom section. These steps may be performed consecutively (i.e., one after the other), but preferably the steps are performed as part of a continuous process, wherein several steps are performed simultaneously (i.e., at the same time). For example, fluid comprising the solid components may be continuously fed to the bottom section and rest fluid may be continuously drained, so that the solid components comprised in the fed fluid may settle before the rest fluid is drained. The step of collecting the settled components may be performed intermittently, e.g., at regular intervals.

According to some embodiments, the solid components to be separated are precipitates. According to some embodiments, the solid components to be separated are cells. These cells may be freely suspended, or they may be adhering, e.g., to microcarriers.

When the solid components are cells, these cells may be capable of producing a biologically active substance, such as a coagulation factor. In such a case, the cells may have been cultivated in the fluid (e.g., in a cell culture broth fluid) before said fluid (including the cells contained therein) is fed to the bottom section in accordance with the present disclosure. During such prior cultivation, the cells may have produced the biologically active substance. Hence, in this embodiment in accordance with the present disclosure, the fluid that is fed to the bottom section in accordance with the present disclosure may contain said biologically active substance.

In another embodiment of the method for separating solid components from a fluid in accordance with the present disclosure, the bottom section is comprised in (i.e., is part of) the assembly in accordance with the present disclosure. In this embodiment, the step of letting the solid components (e.g., cells) to be separated settle is a step of letting the solid components settle in the at least one sedimentation channel of the inclined plate settler that is part of the assembly in accordance with the present disclosure.

When performing the above method in accordance with the present disclosure, the inventors have found that solid components (e.g., cells) that are contained in a fluid (e.g., in a cell culture broth fluid) can be efficiently separated from said fluid with minimal loss of any components that are dissolved in the fluid, such as biologically active substances. Thus, in accordance with the method of the present disclosure, any components that are dissolved in the fluid can be efficiently harvested together with the solid-depleted fluid phase. Accordingly, the present disclosure provides an improved method for separating solid components from a fluid.

Additional advantages and features of the present disclosure, that can be realized on their own or in combination with one or several features discussed above, insofar as the features do not contradict each other, will become apparent from the following description of particular embodiments.

BRIEF DESCRIPTION OF THE DRAWINGS

For a better understanding of the present disclosure and to show how the same may be carried into effect, reference will now be made, by way of example only, to the accompanying drawings, in which:

The description is given with reference to the accompanying drawings, in which:

FIG. 3 is a schematic three dimensional perspective view of an embodiment of a bottom section and, more generally, of an assembly with a plate settler in accordance with the present disclosure;

FIG. 4 is a sectional view of an inlet channel, a collection channel, and a wash fluid supply channel of an embodiment of a bottom section in accordance with the present disclosure;

FIG. 9A is a schematic representation of a split in a flow distributor that is part of an embodiment of a bottom section in accordance with the present disclosure;

FIG. 9B is a schematic representation of a split in a flow distributor that is part of an embodiment of a bottom section in accordance with the present disclosure;

FIG. 9C is a schematic representation of a split in a flow distributor that is part of an embodiment of a bottom section in accordance with the present disclosure;

FIG. 9D is a schematic representation of a split in a flow distributor that is part of an embodiment of a bottom section in accordance with the present disclosure;

FIG. 9E is a schematic representation of a split in a flow distributor that is part of an embodiment of a bottom section in accordance with the present disclosure;

FIG. 9F is a schematic representation of a split in a flow distributor that is part of an embodiment of a bottom section in accordance with the present disclosure;

FIG. 10 is a schematic representation an embodiment of a bottom section and, more generally, of an assembly with a plate settler in accordance with the present disclosure;

FIG. 11 is a schematic representation an embodiment of a bottom section in accordance with the present disclosure;

FIG. 12 is a schematic representation an embodiment of a bottom section in accordance with the present disclosure; and FIG. 13 is a schematic representation an embodiment of a bottom section and, more generally, of an assembly with a plate settler in accordance with the present disclosure.

FIG. 1 depicts an embodiment of a bottom section 1 in accordance with the present disclosure. The bottom section 1 is connected to an embodiment of an assembly 2 for separating a solid component from a fluid in accordance with the present disclosure.

Figures 1, 2:
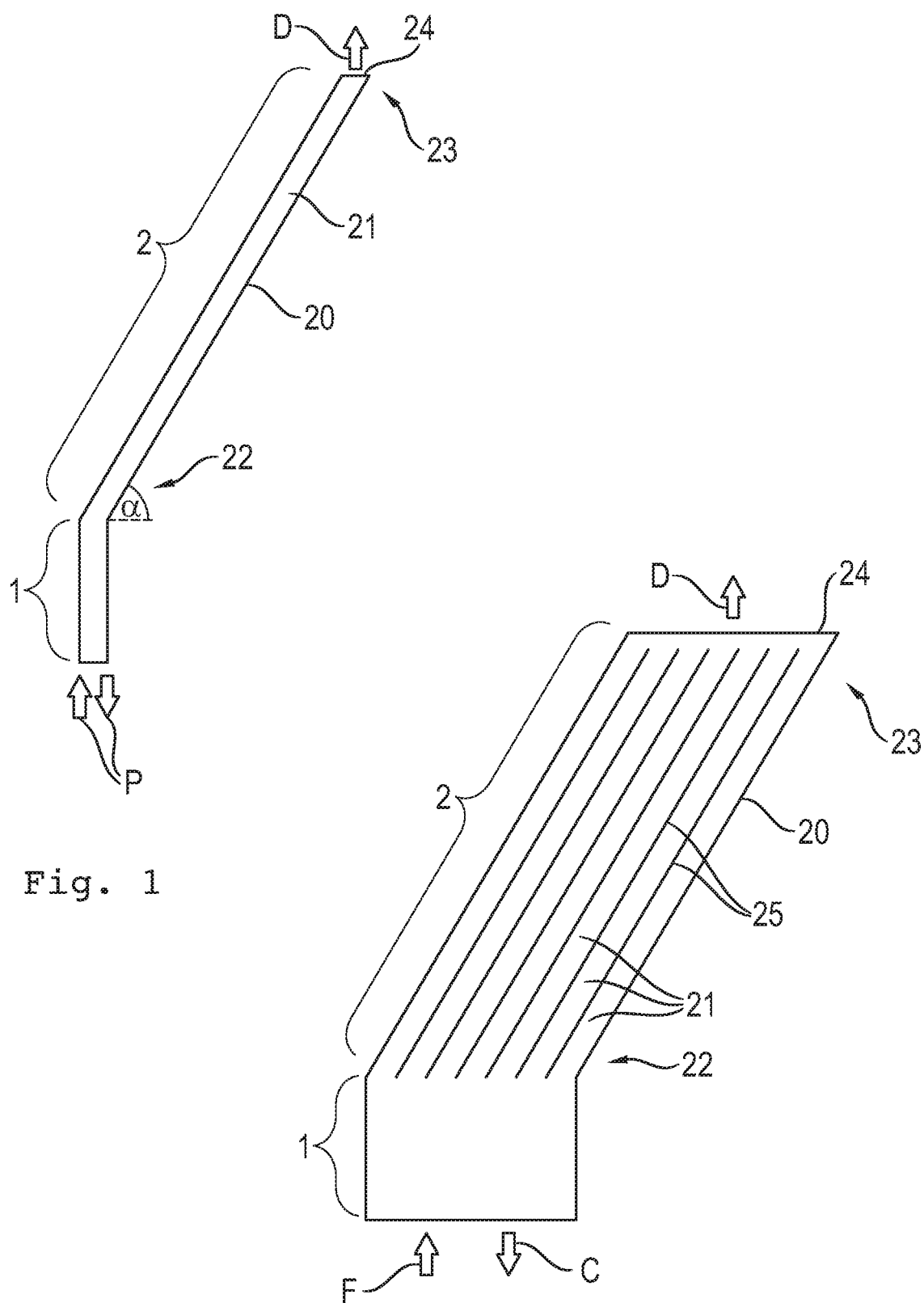
FIG. 1 is a sectional view of a schematic representation of an embodiment of a bottom section in accordance with the present disclosure.
FIG. 2 is a sectional view of a schematic representation of an embodiment of a bottom section in accordance with the present disclosure.

The assembly 2 includes an inclined plate settler 20. It is referred to as inclined because it extends at an angle α with respect to the direction of gravity (the vertical direction in FIG. 1).

This embodiment of the plate settler 20 includes one sedimentation channel 21 for letting a fluid to be separated (e.g., a solid component to be separated) settle. The inclined plate settler 20 has an inclination angle α that is adapted to the densities of the fluid fed to the plate settler 20 and to the density (specific weight, etc.) of the component to be separated (in this case: a solid component on the bottom of the sedimentation channel 20).

The angle α of inclination of the plate settler 20 with respect to the direction of gravity of various embodiments of assemblies and bottom sections in accordance with the present disclosure may lie between 5° and 85°.

The plate settler 20 comprises a lower portion 22 and an upper portion 23. The sedimentation channel 21 extends from the lower portion 22 to the upper portion 23. The bottom section 1 is connected to the lower portion 22. The upper portion 23 is connected to a fluid outlet 24. Rest fluid, from which the fluid (in this case: the precipitated solid component) has been (at least in part) separated, is drained from the upper portion 23 through the fluid outlet 24. The fluid leaving the outlet 24 (and its directions) is symbolized by the arrow D in FIG. 1 ("D" stands for "drain").

Fluid (including the component to be separated) is fed to the assembly 2 through the bottom section 1 from the bottom end. The separated component is also collected through the bottom end. This is symbolized by the double arrow P in FIG. 1.

The bottom section 1 of FIG. 1 is separable from the assembly 2. However, the disclosure also encompasses bottom sections 1 that are integrally formed together with the assembly 2 (assembly 2 and bottom section 1 are made as one piece). The connection between assembly 2 and bottom section 1 in accordance with some embodiments may be reversible, and it may be irreversible for other embodiments.

FIG. 2 depicts another embodiment of a bottom section 1 in accordance with the present disclosure. The bottom section 1 is connected to an embodiment of an assembly 2 for separating a solid component from a fluid in accordance with the present disclosure.

The assembly 2 includes an inclined plate settler 20. This embodiment of the plate settler 20 includes several sedimentation channels 22 for letting a component to be separated settle.

The plate settler 20 comprises a lower portion 22 and an upper portion 23. The sedimentation channels 21 extend from the lower portion 22 to the upper portion 23. The bottom section 1 is connected to the lower portion 22. The upper portion 23 is connected to a fluid outlet 24. Rest fluid, from which the fluid (in this case: the precipitated solid component) has been (at least in part) separated is drained from the upper portion 23 through the fluid outlet 24. The fluid leaving the outlet 24 (and its directions) is symbolized by the arrow D in FIG. 2 ("D" stands for "drain").

Neighboring sedimentation channels 21 are separated by separating walls 25.

Fluid (including the component to be separated) is fed to the assembly 2 through the bottom section 1 from the bottom end. The arrow F symbolizes the fluid being fed ("F" stands for "fed"). The separated component is also collected through the bottom end. This is symbolized by the arrow C in FIG. 2 ("C" stands for "collect").

The bottom section 1 of FIG. 2 is separable from the assembly 2. However, the disclosure also encompasses bottom sections 1 that are integrally formed together with the assembly 2 (assembly 2 and bottom section 1 are made as one piece). The connection between assembly 2 and bottom section 1 in accordance with some embodiments may be reversible, and it may be irreversible for other embodiments.

FIG. 3 is a schematic three dimensional perspective view of an embodiment of a bottom section 1 in accordance with the present disclosure. The bottom section 1 is connected to an embodiment of an assembly 2 for separating a solid component from a fluid in accordance with the present disclosure.

The assembly 2 comprises a plate settler 20. FIG. 3 shows only two sedimentation channels 21 in order not to clutter the schematic representation, however, the number of sedimentation channels 21 may be higher (e.g., a lot higher).

The width w of sedimentation channels 21 may generally for embodiments of the assembly 2 in accordance with the present disclosure lie in a range of 5 cm to 200 cm, optionally a range of 40 cm to 150 cm. The height h of the settling plates (the bottom surfaces of the sedimentation channels 21) may generally lie in a range of 10 cm to 200 cm. The distance d between two settling plates may generally lie in a range of 0.3 cm to 10 cm.

The settling plates (bottom walls) of the sedimentation channels 21 of this embodiment comprise stainless steel that is optionally electropolished (to a resolution of equal to or less than 0.8 μm). According to some embodiments, the settler plates consist of stainless steel. Alternatively, they may comprise or consist of a plastic such as acrylic glass (e.g., polymethyl methacrylate (PMMA) and/or polyethylene terephtalate glycol-modified (PETG)).

The bottom section 1 in accordance with this embodiment is made of stainless steel and/or plastics, and is assembled from layers. Alternatively, it can be made by additive manufacturing (e.g., 3D-printing). However, all of these features may be present in some embodiments and absent from others.

The bottom section 1 of FIG. 3 comprises several inlet channels 10 for feeding a fluid comprising the solid component to be separated to the plate settler 20. The bottom section 1 also comprises several collection channels for collecting a settled solid component descending from the sedimentation channels 21. Other embodiments comprise only one collection channel 11 and/or only one inlet channel 10.

The inlet channels 10 and the collection channels 11 are provided in pairs in the sense that there is one of each of these two channels connected to a corresponding sedimentation channel 21 of the plate settler 20.

Each of the inlet channels 10 and the collection channels 11 are connected to one corresponding sedimentation channel 21, to form fluid connections. The inlet channels 10 and the collection channels 11 are fluidly separated in the sense that there is no direct fluid connection between them within the bottom section 1. They are separated by a wall. An indirect fluid connection via the sedimentation channel 21, however, exists (this way, the separated solid component may return downward in FIG. 3 from the plate settler 20).

The feed angle φ between the inlet channels 10 and the sedimentation channels 21 is in this case 90°. Put differently, end portions of the inlet channels 10 proximate to the plate settler 20 extend in the direction of gravity.

Moreover, also end portions of the collection channels 11 proximate to the plate settler 20 extend in the direction of gravity.

According to other embodiments, the angle φ may lie in a range of 5° and 90°, optionally in a range of 15° and 75°, or in a range of 30° and 60°. The angle φ may also be identical or similar to the inclination angle α of inclination of the plate settler 20. When the angle φ is smaller than 90°, the main part of the supply channel may, e.g., extend in the direction of gravity, and a portion proximate to the end (or the end portion) to be connected to a sedimentation channel may have a portion where the inclination of the supply channel changes. For example, there may be provided a bend (e.g., with an edge) in the supply channel, or the supply channel may comprise a curved portion, so that the angle of extension with respect to a horizontal plane transitions from 90° to an angle φ smaller than 90°.

The fluid separation (i.e., the absence of a direct fluid communication) between inlet channels 10 and collection channels 11 promotes a better control over the behavior of fluid flows in the bottom section 1. Specifically, turbulences arising from mixtures of fluid being supplied and the descending separated solid component (e.g., a precipitate) and/or a descending separated fluid (e.g., comprising a solid component to be separated) in the bottom section 1 or by virtue of the bottom section 1 may be lowered or even avoided. Thus, the efficiency of the separation process may be increased by the bottom section 1 in accordance with these embodiments.

The flow connection between the inlet channels 10 and the corresponding sedimentation channels 21 and the collection channels 11 and the corresponding sedimentation channels 21, respectively, is separate from fluid connections between all other sedimentation channels 21 and all other inlet channels and collection channels 11, respectively. This way, turbulent flows and/or other flow disturbances in the bottom section 1 associated with the pair of channels comprising the respective inlet channel 10 and collection channel 11 and the corresponding sedimentation channel 21 and other channel pairs may be lowered or even fully avoided. This may further increase the efficiency of an assembly 2 connected to the bottom section 1.

The bottom section 1 of FIG. 3 comprises one individual collection channel 12 and one individual inlet channel 11 for each of the plurality of sedimentation channels 21, wherein a separate fluid connection is formed for each corresponding pair of inlet channel 10 and sedimentation channel 21 and for each corresponding pair of collection channel 11 and sedimentation channel 21, respectively. This may lead to a particularly high efficiency of the assembly 2 comprising the plate settler 20 combined with the bottom section 1. Specifically, flow disturbances associated with neighboring pairs of channels 10, 11, 21 may be minimized.

In order to keep the schematic representation of FIG. 3 simple, the figure does not distinguish between the collection channel 11 and respective corresponding wash fluid supply channels 12. The wash fluid supply channels 12 are located between the inlet channels 10 and the collection channels 12. Wash fluid is fed through the wash fluid supply channels 12 and is used to increase the efficiency of the draining of the separated component through the collection channels 11. FIG. 4 shows in more detail how the triplets of inlet channel 10, collection channel 11, and wash fluid supply channel 12 are configured.

The wash fluid supply channels 12 more generally may be used to supply a wash fluid to one or several sedimentation channels 21 or to one or several 12 collection channels directly. The wash fluid supply channels 12 are fluidly separated from other wash fluid supply channels 12 and from all inlet channels 10.

This is shown, e.g., in FIG. 4.

Being fluidly separated from other wash fluid supply channels 12 and from the inlet channels 10 may lower or even avoid the occurrence of efficiency lowering flow disturbances such as, e.g., turbulences associated with neighboring channels 12. The fluid separation pertains to the bottom section 1 itself, but does not mean that there is no indirect fluid connection via, e.g., a connected plate settler 20.

The wash fluid may promote the efficiency of a separation process. For example, when a solid component tends not to be drained efficiently, possibly because there is a tendency to adhere permanently or temporarily to parts of a sedimentation plate or, e.g., to a collection channel 11, supplying the wash fluid may play a sufficient contribution to collect the solid component and to wash it out in one or several collection channels 11 of the bottom section 1.

As can be seen in FIG. 4, the corresponding wash fluid supply channels 12 and collection channels 11 (together corresponding to the same sedimentation channel 21) are fluidly connected by an opening 14 in a wall portion 15 shared by said wash fluid supply channel 12 and said collection channel 11. The fluid connection may be direct in the sense that the fluid connection may exist within the bottom section 1. This may inhibit or even prevent a supplied wash fluid accidentally being guided along the sedimentation channel 21 and being drained out of the top end. The fluid connection in the bottom section 1 may increase the efficiency of a process of washing out a separated fluid or solid component and to collect it via the collection channels 11. It may also additionally increase the flow efficiency by inhibiting or preventing flow disturbances, because a wash fluid may directly be guided towards the collection channels 11.

The openings 14 are also shown in FIG. 3. The angle co of the wash fluid outlets (the openings 14) is in this case 90° with respect to the direction of gravity (the vertical direction in FIG. 3). It may alternatively lie in a range of 15° to 90° with respect to a horizontal direction, e.g., it may extend in the same (or a similar direction) as the principal direction of extension of the sedimentation channels 21 of the plate settler 20.

Figure 5:
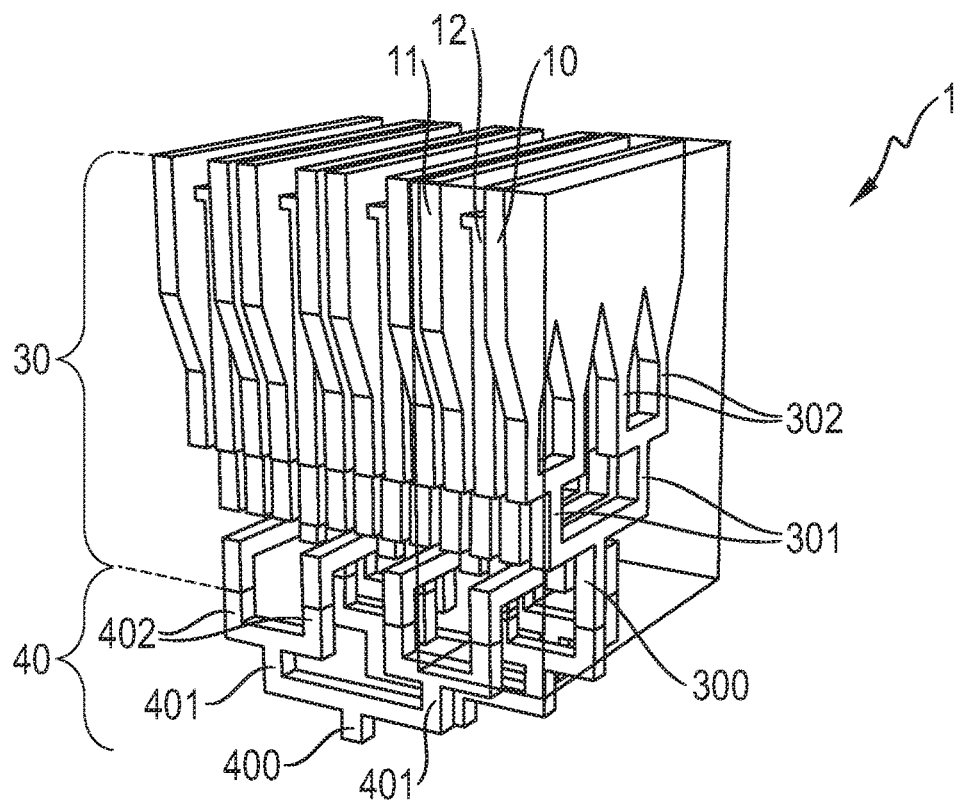
FIG. 5 is a schematic three dimensional perspective view of an embodiment of a bottom section in accordance with the present disclosure.
Figure 6:
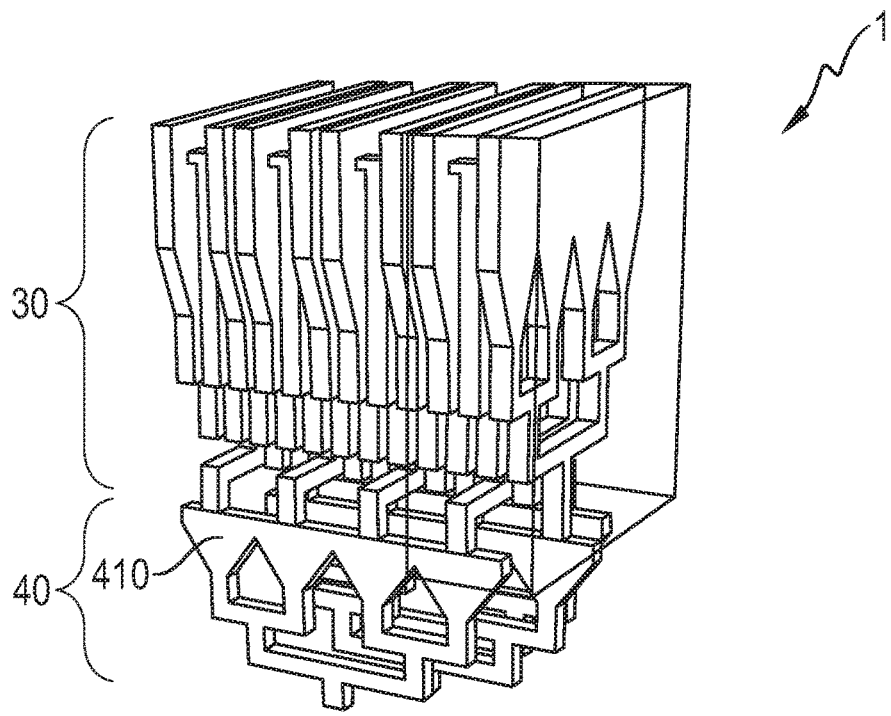
FIG. 6 is a schematic three dimensional perspective view of an embodiment of a bottom section in accordance with the present disclosure.

FIGS. 5 and 6 depict schematic three dimensional views of embodiments of a bottom section 1 in accordance with the present disclosure.

The bottom section 1 of FIG. 5 comprises an intrachannel distributing portion 30 for evenly distributing a fluid flow through the inlet channels 10, the collection channels 11, and the wash fluid supply channels 12, respectively. The intrachannel distributing portion 30 is a fractal flow distributor. The intrachannel distributing portion 30 may increase the efficiency of the use of an assembly 2 connected to the bottom section 1, because it may, e.g., increase the homogeneity of the load applied to corresponding sedimentation channels 21.

The intrachannel distributing portion 30 evenly distributes for all of the inlet channels 10, the collection channels 11, and the wash fluid supply channels 12. In the case of the collection channels 11, the even distribution is to be understood as a form of evenly collecting with respect to the entire diameter of an entire collection channel 11.

For every inlet channel 10, for example, the intrachannel distributing portion 30 comprises a channel 300 that is split into two channels 301, which are then again split into two channels 302 in the direction approaching the portion to be connected to an assembly 2 with a plate settler 20. This can be scaled up in accordance with the desired application and may be referred to as a fractal design of the flow distributor.

The embodiment of FIG. 5 comprises cone-shaped distributing portions which evenly distribute fluid exiting the channels 302 in order to reach the entire cross-section in width direction of the respective inlet channel 10 at a connecting portion to be connected to a plate settler 20.

For every collection channel 11, for example, the intrachannel distributing portion 30 comprises a channel 300 that is split into two channels 301, which are then again split into two channels 302 in the direction approaching the portion to be connected to an assembly 2 with a plate settler 20. This can be scaled up in accordance with the desired application and may be described as being associated with a fractal design of the flow distributor.

Analogous fractal channel arrangements are also provided for each of the collection channels 11 and each of the wash fluid supply channels 12. To avoid repetitions, reference is made to the explanation concerning the channels 300, 301, and 302 for the inlet channels 10.

The bottom section 1 of FIG. 5 also comprises an interchannel distributing portion 40 for evenly distributing a fluid flow in the direction to or the direction from a plate settler over the plurality of inlet channels 11 and over the wash fluid supply channels 12 and over the collection channels 11, respectively. This may further increase the efficiency of the bottom section 1, as it may promote a particularly even flow distribution over all of the present channels, both for fluids supplied to a connected assembly as well as for fluids drained therefrom.

In particular, the interchannel distributing portion 40 is a fractal flow distributor and comprises a distributing portion for all of the inlet channels 10, for all of the collection channels 11, and for all of the wash fluid supply channels 12.

For example, the channel 400 collects fluid from (all of) the collection channels 11. In the direction towards a plate settler 20 connected to the bottom section 1, the channel 400 is split into two channels 401, which are again split into two respective channels 402 each. This illustrates the fractal configuration of the flow distributor. Analogous structure exist for the interchannel distributing portion serving all of the inlet channels 10, and likewise for the interchannel distributing portion serving all of the wash fluid supply channels 12.

The interchannel distributing portion 40 and the intrarchannel distributing portion 30 are connected in series, wherein the intrachannel distributing portion 30 is to be located closer to a connected plate settler 20 than the interchannel distributing portion 40.

An example is explained on how the two serially connected flow distributors work. For every collection channel 11, for example, an intrachannel distributing portion first homogeneously collects fluid (evenly over the cross-section of the collection channel 11). This is done by consecutive uniting of the channels leading from the connecting portion between assembly 2 and bottom section 1 towards the connecting part between the two flow distributors 30, 40. Then, an even collection, evened out over the different intrachannel distributing portions associated with the various collection channels 11, is effected over all of the collection channels by the interchannel distributing portion. Analogous statements hold with respect to the inlet channels 10 and the wash fluid supply channels 12.

FIG. 6 depicts another embodiment of a bottom section 1 comprising an intrachannel distributing portion 30 and an interchannel distributing portion 40. The embodiment is similar to the embodiment of FIG. 5. Reference is therefore made to the explanations provided with regard to FIG. 5, and only differences will be discussed. The interchannel distributing portion 40 of FIG. 6 namely comprise cone-shaped distributing portions 410 at the part of the interchannel distributing portion 40 connected to the neighboring intrachannel disturbing portion 30. Some embodiments comprise these, whereas others do not. The cones are one of several aspects which may contribute to the evening effect of the flow distributor.

More generally, in the fractal flow distributors which are examples of interchannel distributing portions and/or intrachannel distributing portions of bottom sections 1 in accordance with the present disclosure, may comprise channels that are split into two (or more) connecting channels of equal first cross-sections, and said connecting channels are preferably at least once further split into (two or more) respective connecting sub-channels of respective other equal cross-sections. There may be one split, two splits, or several splits.

Figure 7:
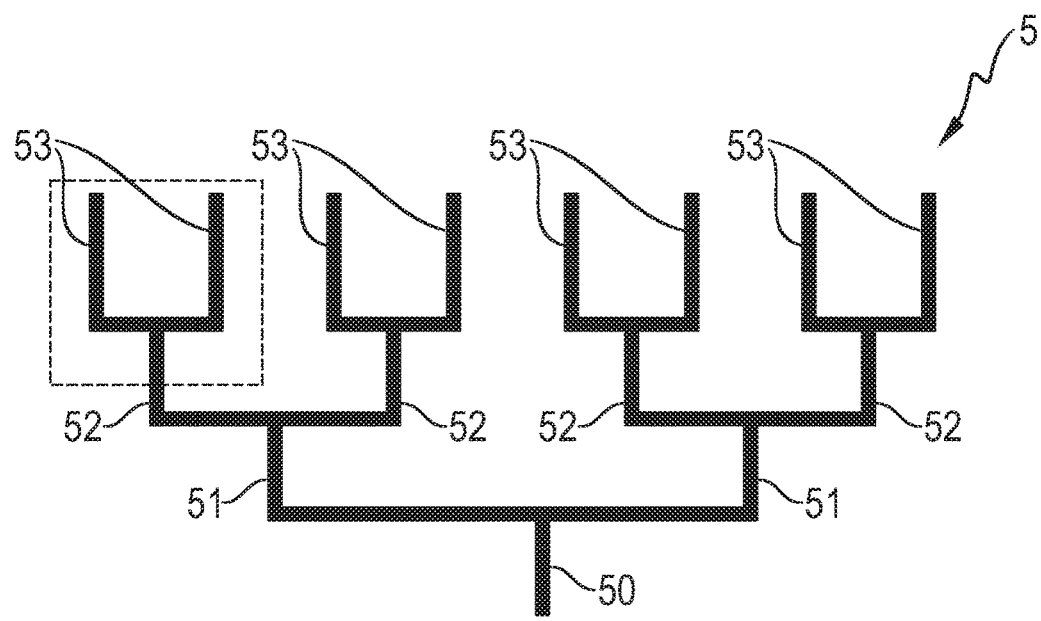
FIG. 7 is a schematic representation of a flow distributor which forms part of an embodiment of a bottom section in accordance with the present disclosure.

FIG. 7 illustrates an example of a flow distributor 5 with three split levels, wherein the splits always are a doubling of the number of channels. Concretely, the channel 50 is split into two channels 51, which are again split into two channels 52 each, wherein each of the channels 52 is again split into two respective channels 53. This can be scaled up as desired in order to scale up an assembly for separating a component of interest from a fluid.

A fractal fluid distributor 5 such as the one illustrated in FIG. 7 may be used for every single inlet channel 10, and/or for every single collection channel 11, and/or for every single wash fluid supply channel 12 of a bottom section 1 in accordance with the present disclosure. This way, the fluid distributor 5 may serve as a (or a part of a) intrachannel distributing portion 30.

The fractal fluid distributor 5 of FIG. 7 may in addition thereto or alternatively be used for several (or for all) inlet channels 10, and/or for several (or for all) collection channels 11, and/or for several (or for all) wash fluid supply channels 12. This way, the fluid distributor 5 may serve as a (or a part of a) interchannel distributing portion 40.

Figures 8A, 8B, 8C:
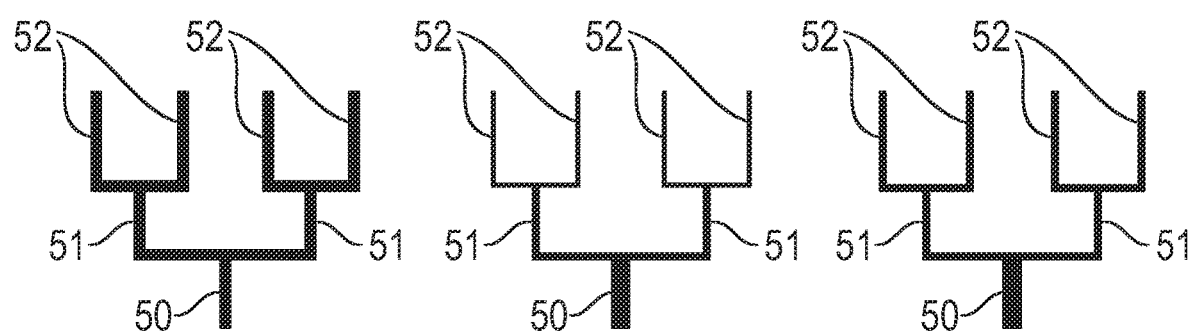
FIG. 8A is a schematic representation of a flow distributor that is part of an embodiment of a bottom section in accordance with the present disclosure.
FIG. 8B is a schematic representation of a flow distributor that is part of an embodiment of a bottom section in accordance with the present disclosure.
FIG. 8C is a schematic representation of a flow distributor that is part of an embodiment of a bottom section in accordance with the present disclosure.

The flow distributor 5 of FIG. 7 is composed such that the cross-section of each channel after a split is identical to the cross-section of a channel before a split. In other words, the cross-section of channel 50 is equal to the cross-section of each of the channels 51, 52, and 53. Such a splitting scheme with equal cross-sections is also illustrated by FIG. 8A.

However, this disclosure encompasses other embodiments. FIG. 8B, for example, discloses a flow distributor splitting scheme, wherein the cross-section of channels is smaller after each split. In other words, in the case of FIG. 8B, the cross-section of channels 52 is smaller than the cross-section of channels 51, and the cross-section of the channels 51 is smaller than the cross-section of channel 50. In contrast, in the case of FIG. 8C, the cross-section is sometimes the same before and after a split, and sometimes it differs between before and after a split. Concretely, the cross-sections of the channels 51 and 52 are of equal size, whereas the cross-section of the channel 50 is larger.

FIGS. 9A to 9F illustrates various possible split geometries that can be used in flow distributors being (part of) an interchannel and/or an intrachannel distributing portion of a bottom section 1 in accordance with the present disclosure.

The splits may be characterized, for example, by two angles β and γ. FIG. 9A shows a configuration of split where β=γ=90°. In the case of FIG. 9B, both β and γ are smaller than 90°. In the case of FIG. 9C, both β and γ are larger than 90°. FIG. 9D shows a case in which the angles β and γ are replaced by a geometry associated with a single angle δ. A split may also be formed by a curve rather than involving some sharp angles, as illustrated by FIG. 9E. In the case of FIG. 9F, two angles β and γ are 90°, but the edges are flattened out so that the shape in the corners is curved. All of these splits may be used as binary splits (splits into two channels) in flow distributors of bottom sections 1 in accordance with the present disclosure. However, also non-binary splits (e.g., splits into three, four, or more channels) may be used.

FIG. 10 schematically depicts two serially connected fractal flow distributors as an intrachannel distributing portion 30 and an interchannel distributing portion 40 of a bottom section 1 connected to an assembly 2 with an inclined plate settler 20. The intrachannel distributing portion 30 and the interchannel distributing portion 40 are rotated by 90° with respect to one another, so that the width directions are perpendicular to one another. Consequently, one can see the splitting up in stages of the interchannel distributing portion 40 in FIG. 10, whereas the components of the intrachannel distributing portion 30 appear as lines in FIG. 10.

The connection between the two flow distributors may, as in the case of FIG. 10, be in the form of cone-shaped extensions so that one integral connecting zone is provided. Alternatively, the connection zone may be present but without any cone-shaped portions, as illustrated by FIG. 11. Another example is shown in FIG. 12, where there is no fluid connection between the different parts of the interchannel distributing portion 40 that are connected to an intrachannel distributing portion 30.

FIG. 13 shows another example of the serial connection of two fractal flow distributors as an intrachannel distributing portion 30 and an interchannel distributing portion 40, wherein there is a 90° rotation in-between (as described with respect to the assembly of FIG. 10). In the case of FIG. 13, another 90° rotation is effected within the intrachannel distributing portion 30, before the last split level. In other words, a split into two channels is provided in a perpendicular direction to the previous splits at the part of the intrachannel distributing portion 30 located closest to the plate settler 20 of the connected assembly 2. The last split into two channels 60 in a perpendicular direction may be particularly useful, for example, when very large solids are to be separated from a fluid, as the widths of the collecting zones may then be rather large. The width split in half may make the suctioning of solids from the collection zone more efficient.

Some embodiments of bottom sections 1 and/or assemblies 2 in accordance with this disclosure may be used such that a relative difference between hydrostatic pressures in different sedimentation channels does not exceed a threshold of 10%. Optionally, the difference does not exceed a threshold of 5%, and optionally it does not exceed a threshold of 3%. These thresholds may (to an increasing degree with a lower threshold value) ensure very similar (or even substantially or fully identical) hydrostatic pressures in different sedimentation channels. This promotes a homogeneous and equilibrated use of the assembly and thus a higher efficiency, because it may make optimal use of the assembly's capacity.

A maximum linear velocity in a channel of a flow distributor (of the intrachannel and/or interchannel distributing portion(s)) may be 1 ml/min/cm plate width of volumetric flow rate during solid removal (and wash flow), up to 50 ml/min/cm plate width. The Reynolds number of the fluid at the top outlets of the upper flow distributor (closest to the plate settler) may be lower than 2000. A length of a fluid channel of a flow distributor may be in the range of 0.5 cm to 5 cm.

The present disclosure also relates to a method for separating solid components from a fluid. Said method comprises a step of feeding fluid comprising the solid components to the at least one inlet channel of the bottom section of the present disclosure; a step of letting the solid components settle; a step of draining (i.e., collecting) the rest fluid (i.e., the solid-depleted fluid); and a step of collecting the settled components through the at least one collection channel of said bottom section. Preferably, in the step of draining the rest fluid the rest fluid is not drained directly from the bottom section, but rather from other parts of an assembly which the bottom section may be part of. For example, the rest fluid may be drained through at least one fluid outlet that is connected to at least one sedimentation channel of an assembly which the bottom section may be part of.

According to some embodiments, the solid components to be separated are precipitates. These precipitates may form by chemical reactions in the fluid, and may already be present in solid form in the fluid when it is fed to the bottom section, or may precipitate from the fluid, e.g., in the plate settler in accordance with the present disclosure.

According to some embodiments of the method for separating solid components from a fluid in accordance with the present disclosure, the solid components to be separated are cells. These cells may be any kind of cells, but preferably the cells are mammalian cells, such as Chinese hamster ovarian (CHO) cells, baby hamster kidney (BHK) cells, or human embryonic kidney (HEK) cells. Mammalian cells are routinely used to produce biologically active substances, in particular recombinant proteins, that may be secreted into cell culture broth fluid and can eventually be recovered to be formulated as a pharmaceutically active drug. Accordingly, according to some embodiments of the method in accordance with the present disclosure, the cells in accordance with the present disclosure comprise genetic information encoding a biologically active substance, so that the cells are capable of producing said biologically active substance.

According to some embodiments, the biologically active substance in accordance with the present disclosure is a protein, such as an antibody, a hormone, or a coagulation factor. Preferably, the protein is a recombinant protein. In a particularly preferred embodiment, the biologically active substance is a coagulation factor, such as Factor VII (FVII) or Factor VIII (FVIII). The preferred coagulation factor in accordance with the present disclosure is Factor VIII (FVIII), preferably human FVIII, which may be recombinantly produced, e.g., in CHO cells. FVIII is a trace plasma glycoprotein that is found in mammals and is involved as a cofactor of Factor IXa in the activation of Factor X. An inherited deficiency of Factor VIII results in the bleeding disorder haemophilia A, which can be treated successfully with purified Factor VIII. Such purified Factor VIII can be extracted from blood plasma, or can be produced by recombinant DNA-based techniques.

In another embodiment of the method for separating solid components from a fluid in accordance with the present disclosure, settled components are collected by pumping a wash fluid to at least one collection channel of the bottom section and by pumping the settled components and the wash fluid from at least one collection channel of the bottom section. Such collection may be performed at regular intervals. The frequency of collection (i.e., the intervals) should be adjusted depending, e.g., on the concentration of solid components in the fluid comprising the solid components. When the solid components are cells, also the tendency of these cells to adhere to surfaces should be taken into account when adjusting the frequency of collection. In a particularly preferred embodiment, the wash buffer should have an equal, preferably a higher density than the fluid comprising the solid components to be separated, and a lower density than the solid components. This is to ensure that the solid components can sediment into the wash fluid and to reduce mixing of the wash fluid with the fluid in accordance with the present disclosure. When the fluid comprising the solid components is a cell culture broth fluid and the solid components are cells, the wash fluid may comprise 14 g/L sodium chloride, 0.2 g/L potassium dihydrogen phosphate, 1.15 g/L sodium dihydrogen phosphate, and have a pH of 7.

According to some embodiments of the method for separating solid components from a fluid in accordance with the present disclosure, the bottom section is comprised in (i.e., is part of) the assembly in accordance with the present disclosure. In this embodiment, the step of letting the solid components (e.g., cells) to be separated settle is a step of letting the solid components settle in the at least one sedimentation channel of the inclined plate settler that is part of the assembly in accordance with the present disclosure. In this embodiment, the rest fluid (i.e., the solid-depleted fluid) may be drained at the upper portion of the at least one sedimentation channel that is part of the plate settler in accordance with the present disclosure, e.g., through at least one fluid outlet that is connected to the at least one sedimentation channel.

When performing the method for separating solid components from a fluid in accordance with the present disclosure, the inventors have found that solid components (e.g., cells) that are contained in a fluid (e.g., a cell culture broth fluid) can be efficiently separated from said fluid with minimal loss of any components that are dissolved in the fluid, such as biologically active substances. Accordingly, according to some embodiments, the amount of solid components in the drained rest fluid is less than 20%, preferably less than 10%, most preferably less than 5% of the amount of solid components in the fluid that is fed to the at least one inlet channel of the bottom section. In another embodiment, the amount of biologically active substance in the drained rest fluid is more than 80%, preferably more than 90%, most preferably more than 95% of the amount of biologically active substance in the fluid that is fed to the at least one inlet channel of the bottom section. The amount of solid components in a fluid preferably refers to the concentration (e.g., in volume per volume) of solid components in said fluid. The skilled person will be aware of various methods to determine such concentration. For example, (relative) concentrations of solid components in a fluid can be determined by turbidity measurements. The amount of biologically active substance in a fluid preferably refers to the concentration (e.g., in weight per volume or in activity units per volume) of biologically active substance in said fluid. The skilled person will be aware of various methods to determine such concentration. For example, FVIII concentration in weight per volume can be determined by antigen ELISA. FVIII concentration in activity units per volume (i.e., FVIII activity) can be determined by chromogenic assays. Such chromogenic assays allow the determination of active FVIII, and yield the concentration, e.g., in international units (IU) per mL.

In another embodiment of the method for separating solid components from a fluid in accordance with the present disclosure, the fluid comprising the solid components is continuously fed to the at least one inlet channel of the bottom section. In this embodiment, it is preferable that the rest fluid (i.e., the solid-depleted fluid) is also continuously drained. The skilled person will be aware of how to adjust the volumetric flow rate into the bottom section to ensure that the solid components have sufficient time to settle, e.g., in the at least one sedimentation channel in accordance with the present disclosure. When the method of the present disclosure is used to separate cells from fluid containing a biologically active substance, the continuous feed into the bottom section may be from a bioreactor comprising a continuous cell culture. Such continuous cell culture may be a chemostat, turbidostat or perfusion culture.

The temperature at which the method of the present disclosure is performed is not particularly limited. The skilled person will be aware of how to select an appropriate temperature based on, e.g., the stability of any used materials and of any substances contained in the fluid comprising solid components. However, temperature differences within the assembly that is used for performing the method for separating solid components in accordance with the present disclosure can result in temperature-induced density differences, which can lead to convection and thereby reduce the efficiency of separation between the wash fluid and the rest fluid. Therefore, it is preferable that the method for separating solid components from a fluid in accordance with the present disclosure is performed at a uniform temperature, i.e., that the assembly (comprising, e.g., a bottom section and a plate settler) that is used for performing the method is kept at a set temperature+/−5° C., preferably at a set temperature+/−3° C.

Consistent with the above, the present inventors have found that cell removal from a cell culture broth fluid is particularly efficient when the assembly in accordance with the present disclosure is situated in a cold room with a temperature of between 2° C. and 8° C. Accordingly, according to some embodiments the method in accordance with the present disclosure is performed at a temperature of between 0° C. and 10° C. (i.e., at a set temperature of 5° C.+/−5° C.), preferably at a temperature of between 2° C. and 8° C. (i.e., at a set temperature of 5° C.+/−3° C.). Such temperatures can be reached, e.g., by situating the assembly in a cold room. If, in the method in accordance with the present disclosure, the assembly is connected to a bioreactor, the bioreactor may be operated at a temperature that is different from the temperature at which the method for separating solid components from a fluid is performed. In particular, if the method in accordance with the present disclosure is performed at a temperature of between 0° C. and 10° C. or between 2° C. and 8° C. by situating the assembly in a cold room, the bioreactor is preferably operated at a higher temperature (e.g., 37° C.) and therefore not situated in the cold room.

The use of embodiments of the bottom section and the assembly in accordance with the present disclosure is illustrated by the following examples without being limited thereto.

EXAMPLES

In the presented examples, embodiments of the bottom section in accordance with the present disclosure (and, more generally, embodiments of the assembly in accordance with the present disclosure) were applied for separation of animal cells from an animal cell culture suspension and for separation of a precipitated solid from its fluid phase.

In examples 1 to 3, Chinese hamster ovarian (CHO) cells expressing a recombinant blood coagulation factor VIII (FVIII) were cultured continuously, wherein the CHO cell culture operation temperature was 37° C. On average, the cell culture broth exhibited a starting turbidity of 46.6 FNU. The bioreactor outlet was directly connected to the inlet of the bottom section in the assembly with the inclined plate settler that is schematically represented in FIG. 2. In these examples, the inclined plate settler was inclined by an angle α'=30° with respect to the vertical direction, being perpendicular to the horizontal direction (the direction of gravity). The angle with respect to the horizontal direction was thus 60°. The inclined plate settler was made from stainless steel with surfaces in contact with process fluid being electro polished to Ra<0.6 µm. The internal hold-up volume of the assembly was 803 mL. The settling section was separated into four sedimentation channels, i.e., settling plates (analogous to (21) in FIG. 2), which were separated by separating walls made ((25) in FIG. 2) of stainless steel in examples 1 and 2 and from PMMA in example 3. A wash solution was supplied to and used with the bottom section. The wash solution consisted of 14 g/L sodium chloride, 0.2 g/L potassium dihydrogen phosphate, 1.15 g/L sodium dihydrogen phosphate, pH 7.

The cell culture broth was continuously transported from the bioreactor to the assembly. The clarified fluid, i.e., cell depleted fluid, was continuously collected from the top outlet of the assembly. The separated solids were collected from the collection channels of the bottom section at regular intervals of 60 min. Collection of the separated solids from the solid collection channels of the bottom section was performed by simultaneous action of the wash fluid pump and the collected solids pump at a volumetric flow rate of 62 and 60 mL/min, respectively. The interval for cell collection, or solid collection in general, was optimized depending on the cell count, i.e., solid load, of the cell culture broth. The flow rate for cell collection or solid collection in general, was optimized depending on the characteristics of the solids, which for example could be a tendency of cells to adhere to surfaces, in order to prevent stalling of sedimented solids within the collection channels of the bottom section.

Samples for analysis were taken in regular intervals from the bioreactor and the fluid streams leaving the assembly. Glucose concentration in the fluid phase was determined using a commercial glucose analyzer (stat profile prime device, nova biomedical). Product (FVIII) concentration was determined by a chromogenic assay using the Chromogenix Coatest® SP4 Factor VIII kit. The chromogenic assay allows measurement of the FVIII co-factor activity, wherein it activates factor X to factor Xa together with factor IXa in the presence of phospholipids and calcium. The activated FXa hydrolyses the chromogenic substrate (S-2765), thus releasing the chromogenic group pNA, whose absorbance can be measured at 405 nm. Under the conditions of the assay factor X activation, and thus generation of the chromogenic substance, pNA is dependent on FVIII amount only (cf. Peyvandi, F., Oldenburg, J. & Friedman, K. D.: A critical appraisal of one-stage and chromogenic assays of factor VIII activity; Journal of thrombosis and haemostasis: JTH 14, 248-261 (2016)). The concentration of the analytes, glucose and FVIII, in the streams collected at the top and from the bottom section of the assembly was used to set up a mass balance, where the amount of analyte recovered in a given period was related to the amount produced/present in the bioreactor in the same period. Cell removal was evaluated by turbidity measurement using a Hach 2100Q, which is a portable turbidometer. The turbidometer measures light scattered by a sample in a round cuvette (25 mm diameter, 60 mm height) at an angle of 90 degrees relative to the direction of the incident light, where the light source is a light emitting diode.

Example 1 for "Bottom Section for being Connected to an Assembly with Plate Settler, and Assembly with Plate Settler" (CHO Cell Separation with an Additional Fluid Circuit)

Figure 14:
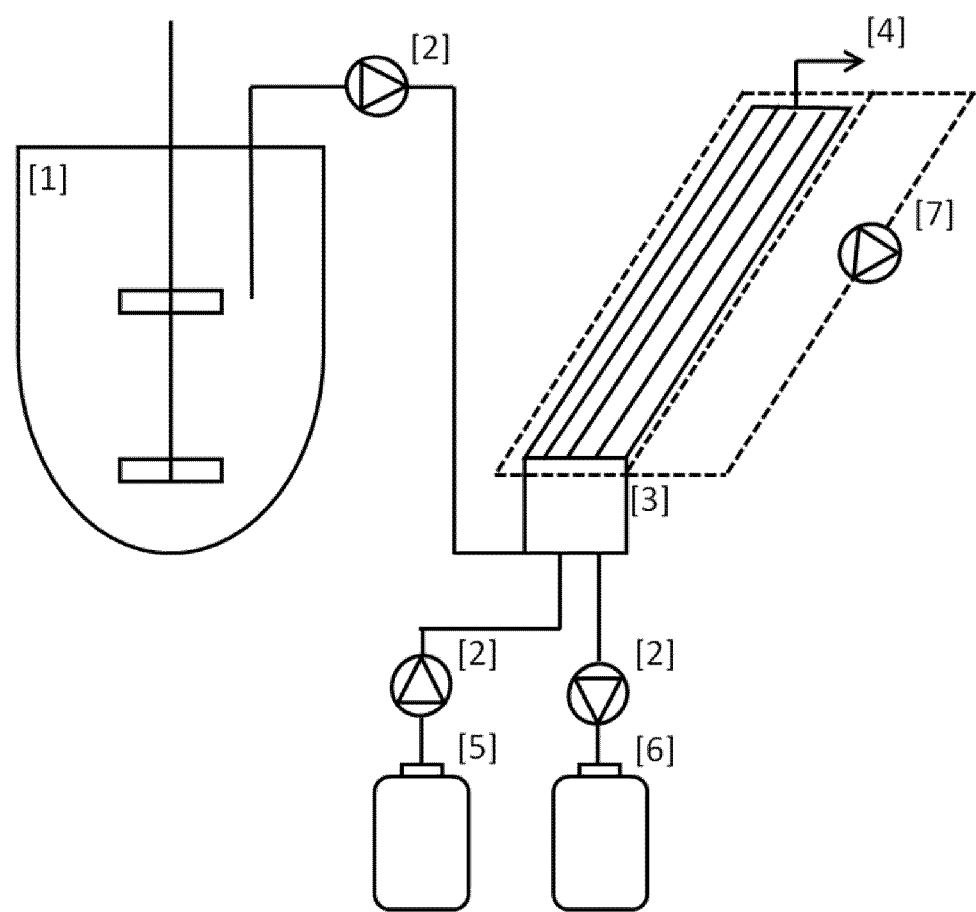
FIG. 14 Schematic drawing of the assembly of bioreactor [1] and inclined plate settler in assembly with the bottom section [3] as used in example 1. The assembly included multiple pumps [2] via which the cell culture broth was transported to the assembly, the wash solution [5] was supplied to the bottom section and the solids (cells) [6] were collected from the bottom section. The clarified fluid was collected at the top outlet of the assembly [4]. The dashed lines indicate the double jacket and the cryostat, which make up an additional fluid circuit [7] that was not fluidly connected to the cell culture broth, the solid depleted fluid or the collected solids (cells).

The inclined plate settler was cooled by a double jacket connected to a cryostat, which was set to 4° C. The double jacket and the cryostat are schematically indicated by the dashed lines with the pump in FIG. 14. The bottom section was not cooled. The single-use bag containing the wash fluid was placed in wet ice for temperature control, thus resulting in a temperature of approx. 0° C. Two runs, which lasted for 49 and 90 hours, respectively, were performed with this mode of temperature control.

Figure 15:
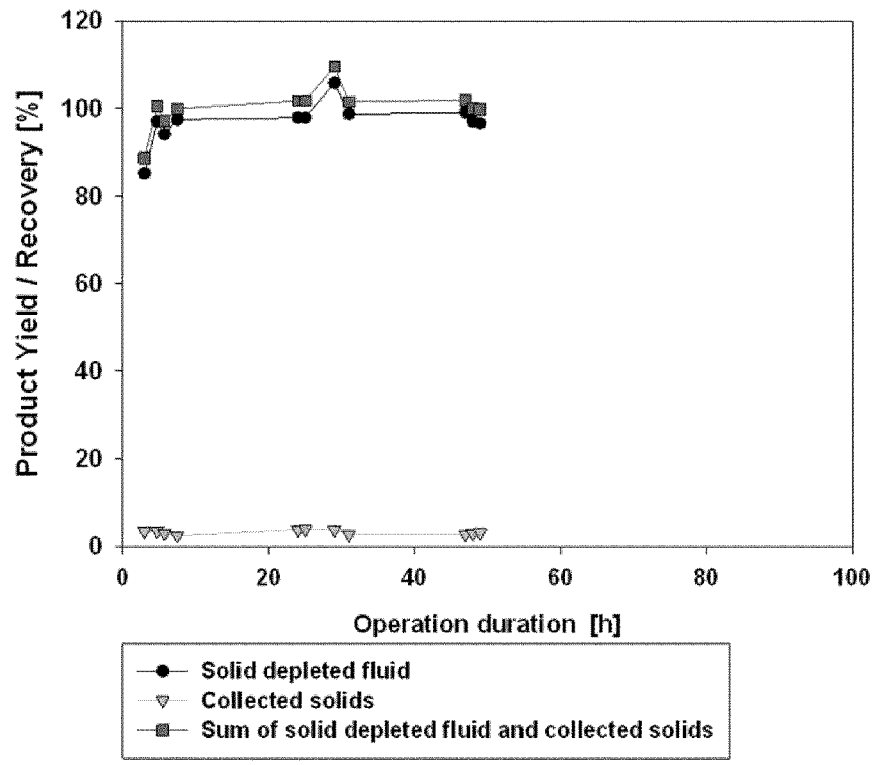
FIG. 15 Product (FVIII) yield and recovery in the fluid streams collected from the top and bottom outlets of the inclined plate settler in assembly with the bottom section under temperature control via double jacket as described by example 1. Recovery=sum of yield in both streams leaving the inclined plate settler and bottom section assembly. The top and bottom panels show the results of two separate runs.
Figure 15:
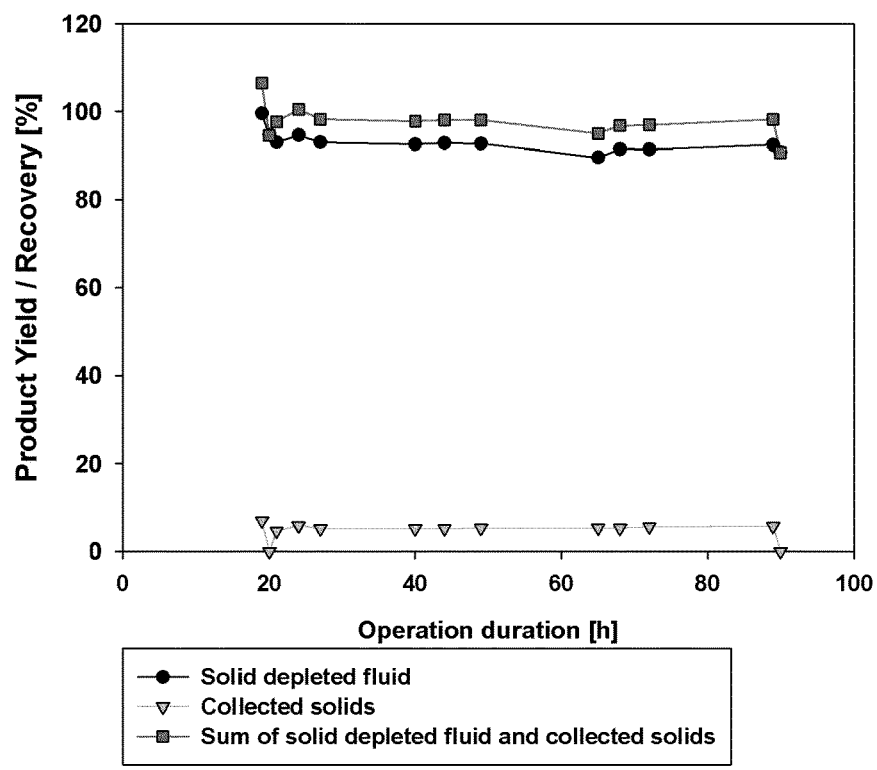
Figure 16:
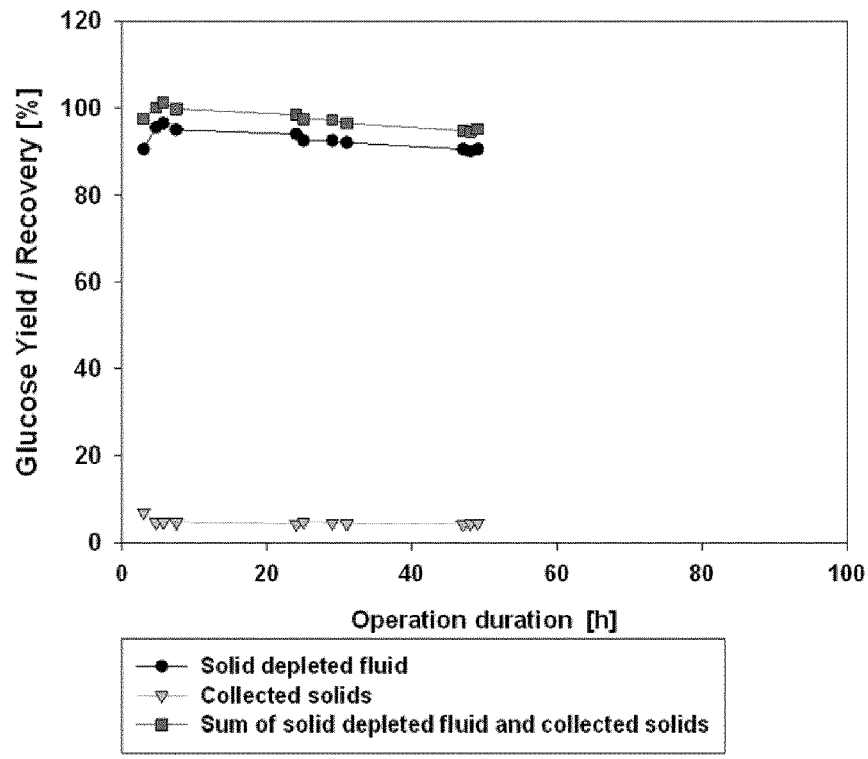
FIG. 16: Glucose yield and recovery in the fluid streams collected from the top and bottom outlets of the inclined plate settler in assembly with the bottom section under temperature control via double jacket as described in example 1. Recovery=sum of yield in both streams leaving the inclined plate settler and bottom section assembly. The top and bottom panels show the results of two separate runs.
Figure 16:
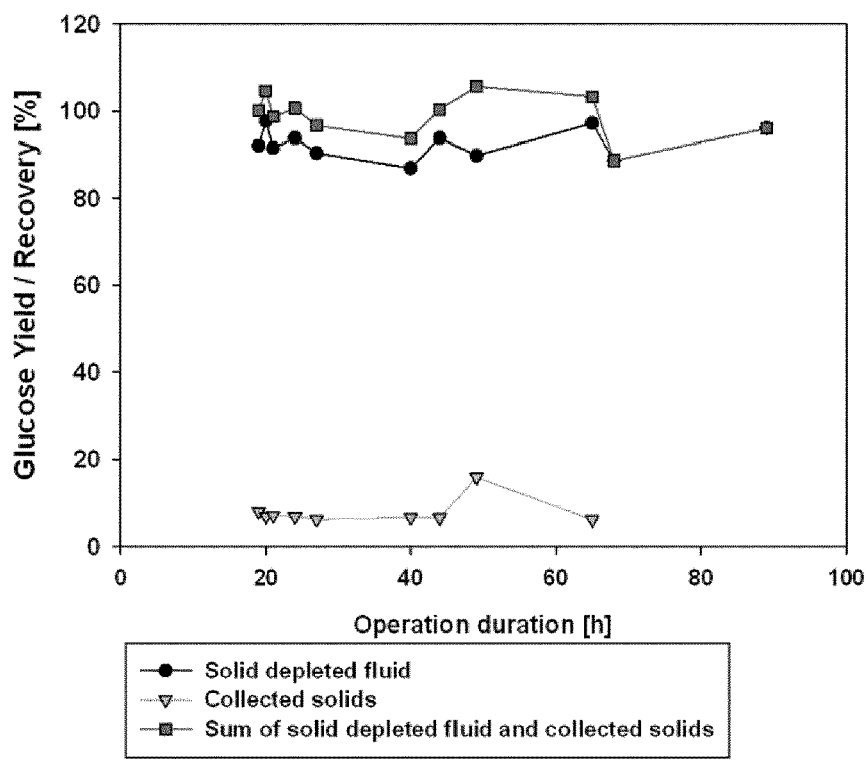

In order to show that the bottom section of the inclined plate settler in accordance with the present disclosure allows to separate cells from the product containing liquid fraction with minimal product loss, glucose and FVIII concentration were measured. In the bottom section, cells were sedimented into the provided wash fluid, while the entire liquid fraction of the culture broth was collected at the top outlet. The wash buffer must have a density higher than the liquid fraction of the culture broth and a density lower than the solids. Thereby, cells can sediment into the wash buffer and minimal mixing of the wash fluid with the culture broth fluid is achieved. In the presented examples, this was the case for the specified wash buffer. Cells could be successfully removed while the product containing fluid fraction could be collected with high yield at the top outlet. The data for FVIII and glucose yield, are plotted in FIG. 15 and FIG. 16, with the values in Table 1 and Table 2. Turbidity as a measure for cell removal can be found in Table 1. Under the conditions in example 1, it is possible to use glucose as an indicator for product (FVIII), because it is not metabolized by the cells.

TABLE 1

Product (FVIII) yield given in percent of amount present in the fluid fraction collected at the bottom and at the top outlet of the assembly in example 1 and turbidity given in FNU measured in the fluid collected at the top outlet in example 1. The turbidity of the cell containing culture broth was 46.6 FNU in average.

| Run 1 | | | | Run 2 | | | |
|---|---|---|---|---|---|---|---|
| Run duration [h] | FVIII Yield at bottom outlet | FVIII Yield at top outlet | Turbidity at top outlet | Run duration [h] | FVIII Yield at bottom outlet | FVIII Yield at top outlet | Turbidity at top outlet |
| 3 | 3.47 | 85.2 | 0.86 | 19 | 6.97 | 99.5 | 6.85 |
| 5 | 3.51 | 97.0 | 0.87 | 20 | below LOD | 94.7 | 1.98 |
| 6 | 3.04 | 94.0 | 0.77 | 21 | 4.62 | 93.0 | 1.03 |
| 8 | 2.48 | 97.4 | 0.95 | 24 | 5.86 | 94.7 | 1.81 |
| 24 | 3.84 | 97.8 | 1.24 | 27 | 5.21 | 93.0 | 2.00 |
| 25 | 3.93 | 97.8 | 0.95 | 40 | 5.24 | 92.6 | 4.87 |
| 29 | 3.76 | 106 | 1.27 | 44 | 5.19 | 92.8 | 1.87 |
| 31 | 2.76 | 98.6 | 1.32 | 49 | 5.30 | 92.8 | 2.71 |
| 47 | 2.79 | 99.1 | 2.06 | 65 | 5.35 | 89.6 | 2.58 |
| 48 | 3.01 | 97.0 | 2.47 | 68 | 5.33 | 91.5 | 4.08 |

TABLE 1-continued

Product (FVIII) yield given in percent of amount present in the fluid fraction collected at the bottom and at the top outlet of the assembly in example 1 and turbidity given in FNU measured in the fluid collected at the top outlet in example 1. The turbidity of the cell containing culture broth was 46.6 FNU in average.

| | Run 1 | | | | Run 2 | | |
|---|---|---|---|---|---|---|---|
| Run duration [h] | FVIII Yield at bottom outlet | FVIII Yield at top outlet | Turbidity at top outlet | Run duration [h] | FVIII Yield at bottom outlet | FVIII Yield at top outlet | Turbidity at top outlet |
| 49 | 3.12 | 96.5 | 2.16 | 72 | 5.65 | 91.4 | 3.23 |
| | | | | 89 | 5.74 | 92.5 | 8.42 |
| | | | | 90 | below LOD | 90.7 | 7.83 |

LOD = limit of detection; 0.2.

TABLE 2

Glucose yield given in percent of amount present in the fluid fraction collected at the bottom and at the top outlet of the assembly in example 1.

| | Run 1 | | | Run 2 | |
|---|---|---|---|---|---|
| Run duration [h] | Glucose Yield at bottom outlet | Glucose Yield at top outlet | Run duration [h] | Glucose Yield at bottom outlet | Glucose Yield at top outlet |
| 3 | 7.05 | 90.5 | 19 | 8.00 | 92.1 |
| 5 | 4.71 | 95.4 | 20 | 6.98 | 97.7 |
| 6 | 4.89 | 96.4 | 21 | 7.15 | 91.5 |
| 8 | 4.81 | 94.9 | 24 | 6.89 | 93.8 |
| 24 | 4.40 | 93.9 | 27 | 6.24 | 90.4 |
| 25 | 4.94 | 92.5 | 40 | 6.69 | 87.0 |
| 29 | 4.71 | 92.5 | 44 | 6.59 | 93.8 |
| 31 | 4.49 | 92.0 | 49 | 15.9 | 89.8 |
| 47 | 4.25 | 90.5 | 65 | 6.18 | 97.2 |
| 48 | 4.51 | 90.0 | 68 | n.d. | 88.7 |
| 49 | 4.65 | 90.5 | 89 | n.d. | 96.0 | n.d. = not determined

Example 2 for "Bottom Section for being Connected to an Assembly with Plate Settler, and Assembly with Plate Settler" (CHO Cell Separation without Additional Fluid Circuit)

Figure 17:
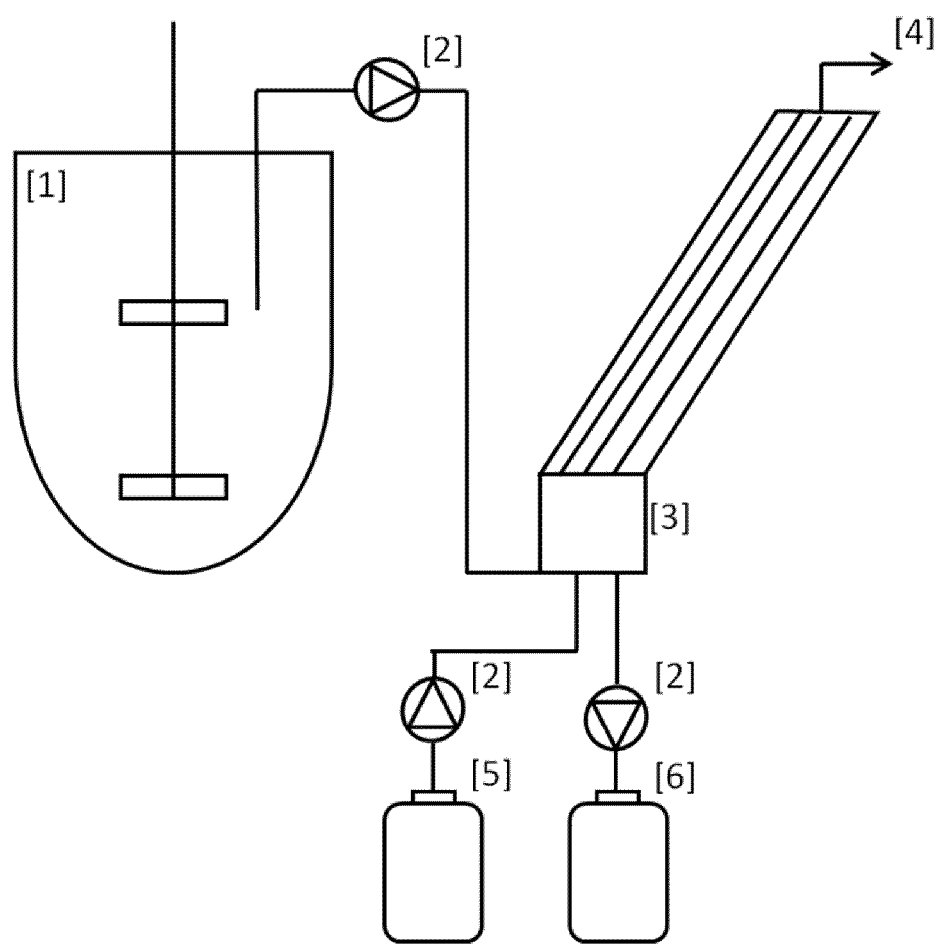
FIG. 17 Schematic drawing of the assembly of bioreactor [1] and inclined plate settler in assembly with bottom section [3] as used in example 2. The assembly included multiple pumps [2] via which cell culture broth was transported to the assembly, the wash solution [5] was supplied to the bottom section and the solids [6] were collected from the bottom section. The clarified fluid was collected at the top outlet of the assembly [4]. The entire setup with exception of the bioreactor was situated in a cold room at 2-8° C.
Figure 18:
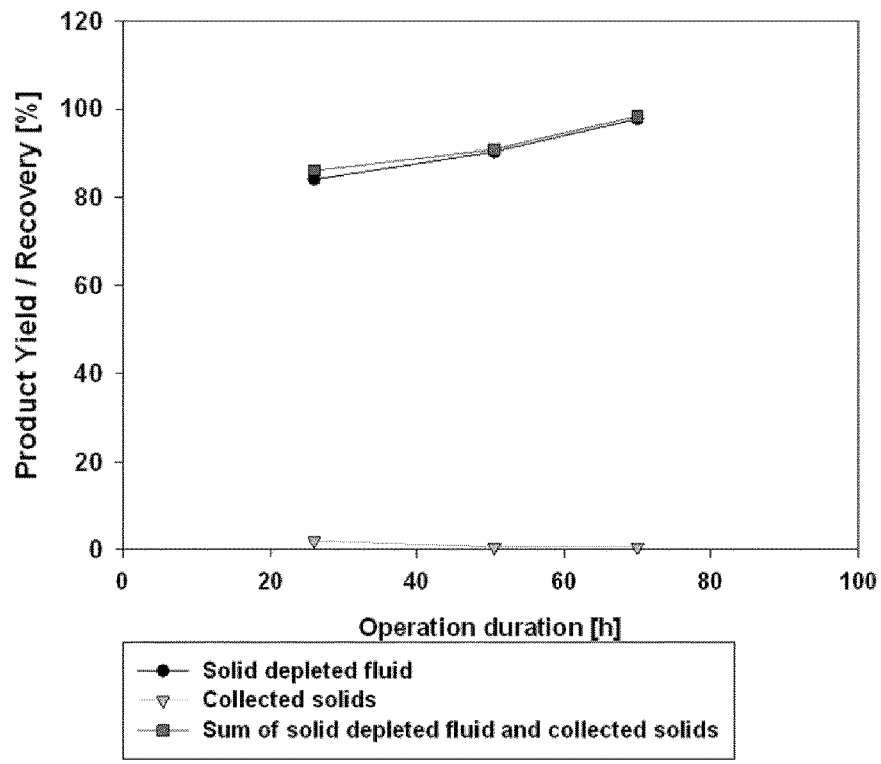
FIG. 18 Product yield and recovery (top) and glucose yield and recovery (bottom) in the fluid streams collected from the top and bottom outlet of the inclined plate settler and the bottom section as described by example 2 (corresponding FIG. 17). Recovery=sum of yield in both streams leaving the inclined plate settler and bottom section assembly.
Figure 18:
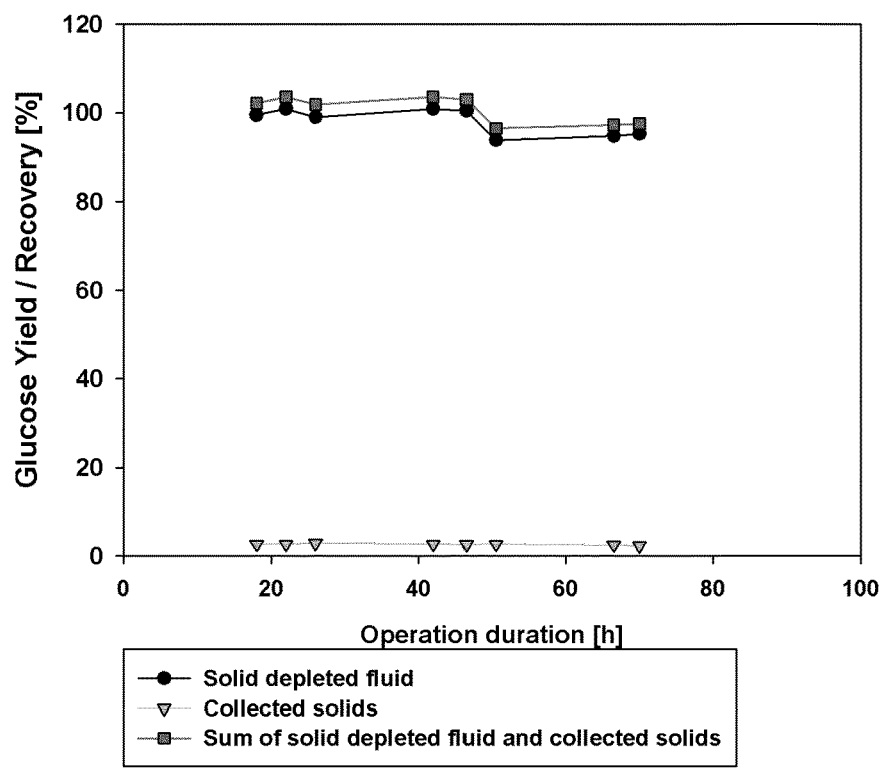

In example 2, the assembly of the inclined plate settler with the bottom section, including all supplying and receiving vessels (except the bioreactor), was set up in a cold room, where the temperature was 2 to 8° C. The setup is schematically depicted in FIG. 17. The inclined plate settler and bottom section were identical to example 1. One run was performed under these conditions which lasted for 70 hours. In order to show that the bottom section of the inclined plate settler in accordance with the present disclosure allows to separate cells from the product containing liquid fraction with minimal product loss, glucose and FVIII concentration were measured. In the bottom section cells were sedimented into the provided wash fluid, while the entire liquid fraction of the culture broth was collected at the top outlet. The wash buffer must have a density higher than the liquid fraction of the culture broth and a lower density than the solids. Thereby, cells can sediment into the wash buffer and minimal mixing of the wash fluid with the culture broth fluid is achieved. In the presented examples, this was the case for the specified wash buffer. Cells could be successfully removed while the product containing fluid fraction could be collected with high yield at the top outlet. The data obtained in example 2 for FVIII and glucose yield are plotted in FIG. 18, with the values for product (FVIII) yield in Table 3 and values for glucose yield and turbidity measured in the samples collected at the top outlet as a measure for cell removal in Table 4. The turbidity data indicated cell removal was more efficient and more stable over time, when the inclined plate settler and bottom section were set up in the cold room as compared to cooling via the double jacket (as described in example 1).

TABLE 3

Product (FVIII) yield given in percent of amount present in the fluid fraction collected at the bottom and at the top outlet of the assembly in example 2.

| Run duration [h] | FVIII Yield at bottom outlet | FVIII Yield at top outlet |
|---|---|---|
| 26 | 2.01 | 84.1 |
| 51 | 0.56 | 90.4 |
| 70 | 0.56 | 97.8 |

TABLE 4

Glucose yield given in percent of amount present in the fluid fraction collected at the bottom and at the top outlet of the assembly in example 2 and turbidity given in FNU measured in the fluid collected at the top outlet in example 2. The turbidity of the cell containing culture broth was 46.6 FNU in average.

| Run duration [h] | Glucose Yield at bottom outlet | Glucose Yield at top outlet | Turbidity at top outlet |
|---|---|---|---|
| 18 | 2.67 | 99.5 | 2.62 |
| 22 | 2.67 | 101 | 0.72 |
| 26 | 2.84 | 99.0 | 0.87 |
| 42 | 2.67 | 101 | 1.38 |
| 47 | 2.58 | 100 | 1.98 |
| 51 | 2.67 | 93.8 | 1.69 |
| 67 | 2.49 | 94.7 | 1.49 |
| 70 | 2.31 | 95.2 | 1.06 |

Example 3 for "Bottom Section for being Connected to an Assembly with Plate Settler, and Assembly with Plate Settler" (CHO Cell Separation with PMMA Physical Barriers)

Figure 19:
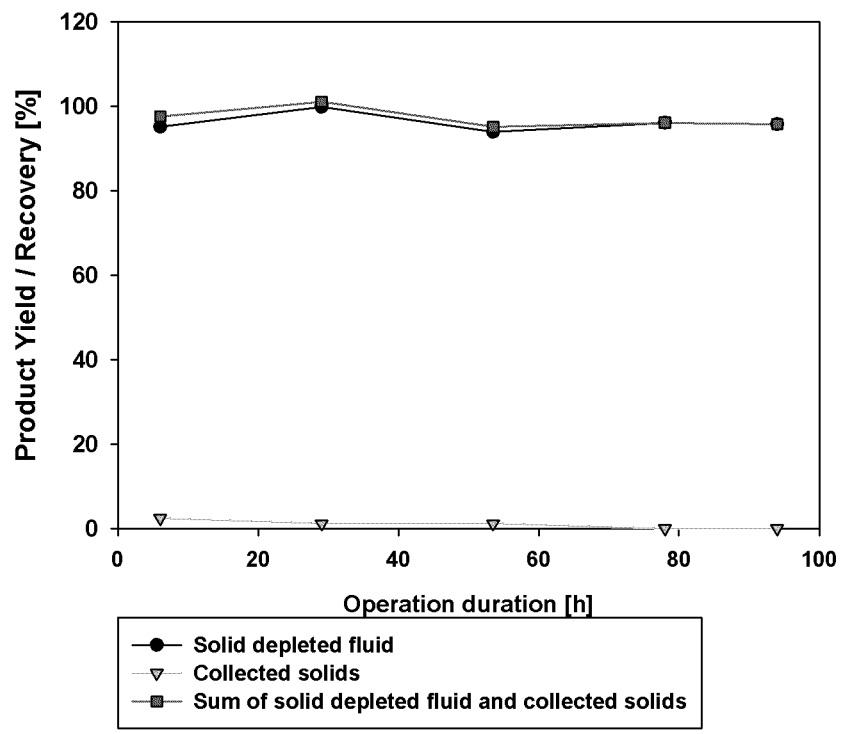
FIG. 19 Product yield and recovery (top) and glucose yield and recovery (bottom) in the fluid streams collected from the top and bottom outlet of the inclined plate settler and the bottom section as described in example 3 (corresponding FIG. 17). Recovery=sum of yield in both streams leaving the inclined plate settler and bottom section assembly.
Figure 19:
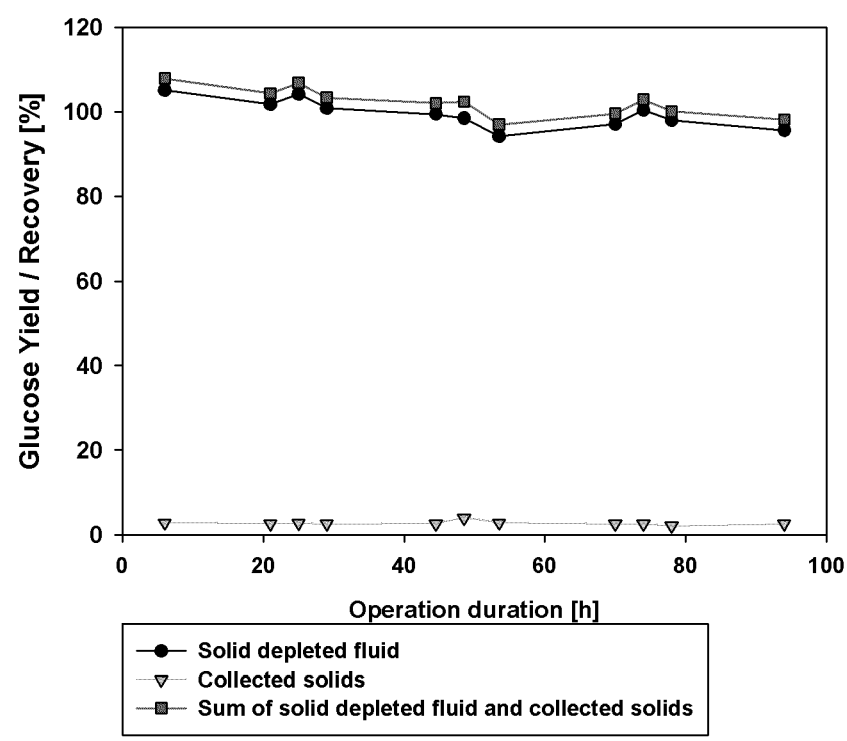

In example 3, the assembly of the inclined plate settler with the bottom section, including all supplying and receiving vessels (except the bioreactor), was set up in a cold room, where the temperature was 2° C. to 8° C. The setup is schematically depicted in FIG. 17. The inclined plate settler was made of stainless steel with surfaces in contact with cell culture broth being electro polished to Ra<0.6 μm. The settling section was separated into four sedimentation channels, i.e. settling plates (analogous to (21) in FIG. 2), which were separated by separating walls made of polymethylmethacrylat (PMMA) ((25) in FIG. 2). One run was performed with this setup, which lasted for 94 hours. In order to show that the bottom section of the inclined plate settler in accordance with the present disclosure allows to separate cells from the product containing liquid fraction with minimal product loss, glucose and FVIII concentration were measured. In the bottom section, cells were sedimented into the provided wash fluid, while the entire liquid fraction of the culture broth was collected at the top outlet. The wash buffer must have a density higher than the liquid fraction of the culture broth and a lower density than the solids. Thereby, cells can sediment into the wash buffer and minimal mixing of the wash fluid with the culture broth fluid is achieved. In the presented examples, this was the case for the specified wash buffer. Cells could be successfully removed while the product containing fluid fraction could be collected with high yield at the top outlet. The data for FVIII and glucose yield are plotted in FIG. 19, with the values for product (FVIII) yield in Table 5 and values for glucose yield and turbidity measured in the samples collected at the top outlet as a measure for cell removal in Table 6. The turbidity data indicate cell removal was more efficient and more stable over time, when the inclined plate settler and bottom section were set up in the cold room as compared to cooling via the double jacket (as described in example 1). There was no difference in separation performance (based on the available data) with regard to the material of the separating walls between example 2 (stainless steel) and example 3 (PMMA).

TABLE 5

Product (FVIII) yield given in percent of amount present in the fluid fraction collected at the bottom and at the top outlet of the assembly in example 3.

| Run duration [h] | FVIII Yield at bottom outlet | FVIII Yield at top outlet |
|---|---|---|
| 6 | 2.43 | 95.2 |
| 29 | 1.18 | 99.9 |
| 54 | 1.18 | 93.9 |
| 78 | below LOD | 96.1 |
| 94 | below LOD | 95.8 |

LOD = limit of detection; 0.2. IU/ml.

TABLE 6

Glucose yield given in percent of amount present in the fluid fraction collected at the bottom and at the top outlet of the assembly in example 3 and turbidity given in FNU measured in the fluid collected at the top outlet in example 3.

| Run duration [h] | Glucose Yield at bottom outlet | Glucose Yield at top outlet | Turbidity at top outlet |
|---|---|---|---|
| 6 | 2.77 | 105 | 1.27 |
| 21 | 2.59 | 102 | 0.93 |
| 25 | 2.68 | 104 | 1.12 |
| 29 | 2.50 | 101 | 0.83 |
| 45 | 2.59 | 100 | 0.92 |
| 49 | 3.93 | 98.6 | 0.92 |
| 54 | 2.77 | 94.3 | 1.54 |
| 70 | 2.50 | 97.2 | 0.82 |
| 74 | 2.50 | 100 | 1.23 |
| 78 | 2.06 | 98.1 | 1.2 |
| 94 | 2.50 | 95.7 | 0.92 |

Example 4 for "Bottom Section for being Connected to an Assembly with Plate Settler, and Assembly with Plate Settler" (Supply and Collection of Process Streams to the Bottom Section for Cleaning in Place)

Figure 20:
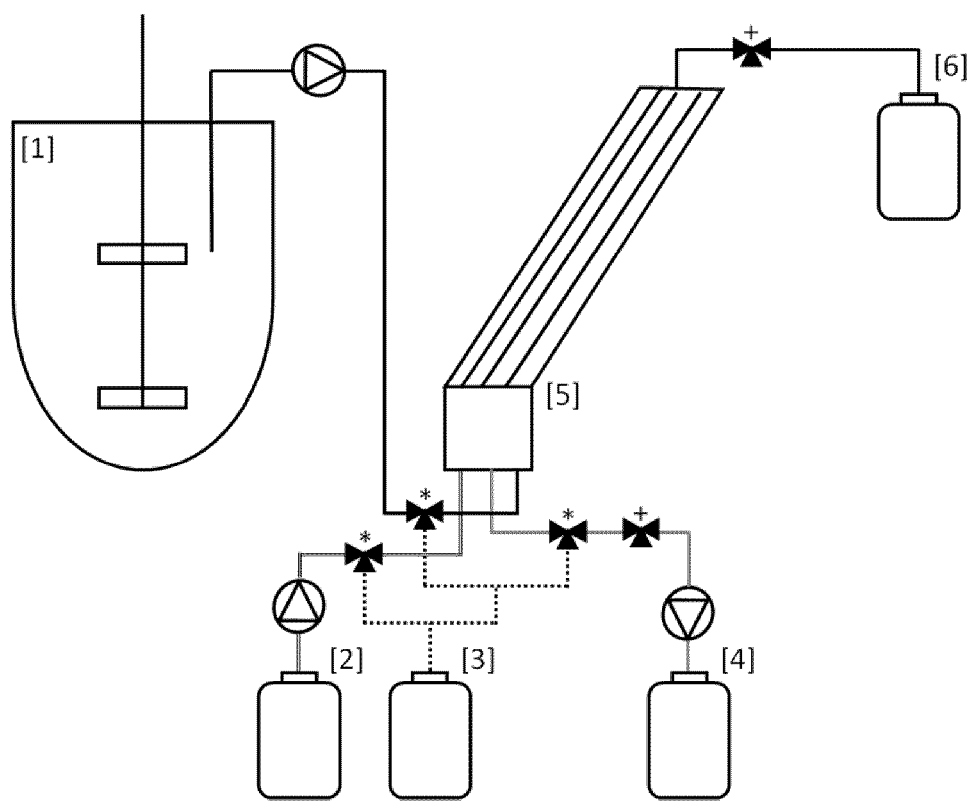
FIG. 20 Schematic drawing of the bottom section in assembly with the inclined plate settler [5] connected to a supplying vessel [1], which could be, a bioreactor or a vessel containing a process fluid such as 1 M sodium hydroxide or buffer. The assembly comprises three-way-valves for switching between different fluid paths (marked with *) and three-way-valves for sampling (marked with +). Further, it comprises a vessel for supply of a wash solution [2], a receiving vessel for, e.g. an exhaust fluid [3], a receiving vessel for the collected solids [4] and a receiving vessel for solid depleted fluid [6]. All receiving vessels comprise an additional connection that encompasses a sterile filter, thus pressure exchange is possible without compromising the aseptic conditions within the assembly.

Example 4 relates to an embodiment of the assembly of the bottom section with an inclined plate settler including switchable connections to supplying and receiving vessels. The inclined plate settler and bottom section with the connected vessels were assembled as a "closed system". The used vessels were multi-use glassware that was autoclaved prior to use. The connecting elements were made from silicone and c-flex tubing, Luer and metal connectors. Silicone tubing and Luer connectors were considered as single-use. However, all vessels and connecting elements could be also be (1) single use and (2) pre-assembled. In the default-state the three-way-valves situated at the bottom section were configured such that a direct fluid connection between vessels [1], [2] and [4] and the assembly was made. For cleaning in place (CIP) 1 M sodium hydroxide solution was pumped from a supplying vessel ([1] in FIG. 20) into the assembly of plate settler and bottom section. The assembly was completely filled and the sampling valves (marked with +) flushed with 1 M sodium hydroxide. The assembly was incubated for at least 15 minutes with 1 M sodium hydroxide. After the incubation time, the three-way-valves situated at the bottom section were switched such that a direct fluid connection between the assembly and a receiving vessel ([3] in FIG. 20) was established. The 1 M sodium hydroxide solution was drained to the receiving vessel by gravity flow. During draining of fluid from the assembly, an inflow of air was provided via receiving vessel [6]. When the assembly was empty, the three-way-valves were switched back to the original position creating a direct fluid connection between vessels [1], [2] and [4] and the assembly and could be filled anew. The filling and draining procedure including the flush of the sampling valves was repeated at least twice with an aqueous buffer solution (e.g. 8 g/L sodium chloride, 0.2 g/L potassium dihydrogen phosphate, 1.15 g/L sodium dihydrogen phosphate, pH 7). Completeness of the CIP procedure was confirmed by pH measurement of samples taken from the sampling valves, where a pH of <7.2 was accepted.

Example 5 for "Bottom Section for being Connected to an Assembly with Plate Settler, and Assembly with Plate Settler" (Separation of a Precipitated Solid at Various Collection Flow Rates in the Presence of an Amino Acid)

In example 5, a precipitate suspension was separated into its solid fraction, i.e. the precipitate, and its fluid fraction, i.e. the precipitation supernatant. The precipitate suspension was produced by supplementation of an aqueous solution comprised of 10 mM Tris(hydroxymethyl)-aminomethan, 100 mM sodium chloride and 100 mg/mL Tryptophan pH 8.5 with 2.7 mM phosphate ions and 15 mM calcium ions. The formed solid phase was non-stoichiometric calcium phosphate. The precipitate suspension was directly and continuously transported to the inlet of the bottom section in assembly with the inclined plate settler. In these examples, the inclined plate settler was inclined at by an angle $\alpha'=30°$ from the vertical direction, i.e., an angle of $\alpha=60°$ with respect to the horizontal direction (the direction of gravity). The inclined plate settler was made from stainless steel where the surfaces in contact with process fluid were electro polished to Ra<0.6 μm. The internal hold-up volume consisting of bottom section and an inclined plate settler with a single settling channel was 630 mL. A wash solution was supplied to and used with the bottom section. The wash fluid was an aqueous solution containing 2 mM Tris(hydroxymethyl)-aminomethan, 252 mM sodium chloride and 6 mM calcium chloride. The wash fluid density must be higher than the density of the fluid in the precipitate suspension and lower than the density of the suspended solids in order for the solids to settle from the fluid they were originally suspended in into the wash buffer provided in the bottom section. For the precipitate suspension and the wash fluid in this example, the densities were matching this criterion.

During operation of the assembly, the solid depleted fluid was continuously collected from the top outlet of the assembly. Separated solids were collected from the collection channels of the bottom section at regular timely intervals of 15 min. Solid collection was achieved by simultaneous action of the wash fluid and the solid collection pump at volumetric flow rates of 20, 40 and 60 mL/min.

Figure 21:
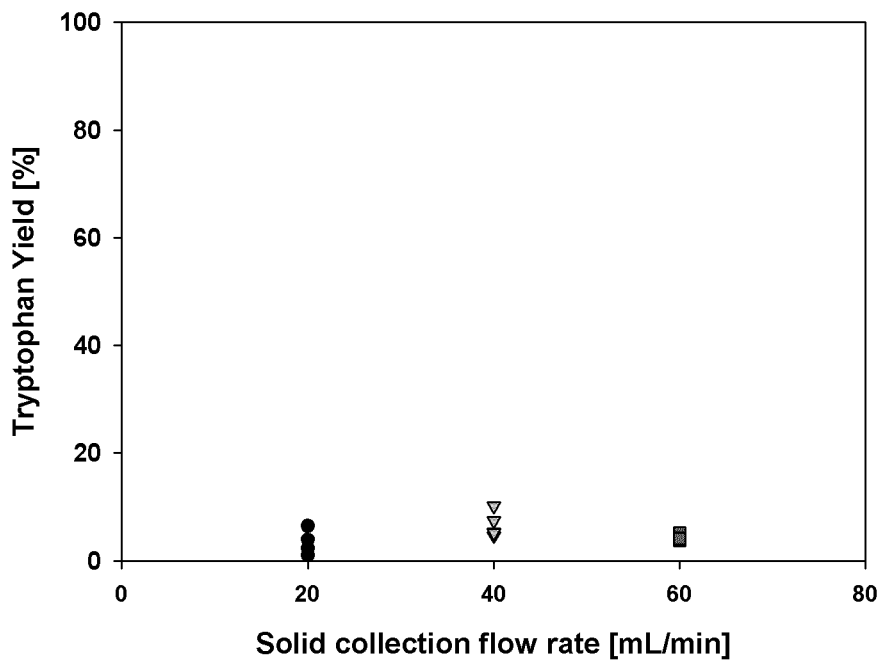
FIG. 21 Yield of Tryptophan in the fraction containing the collected solids (i.e. the precipitate) suspended in wash fluid obtained at varying collection flow rates. Tryptophan was originally comprised in the precipitate suspension.

In order to demonstrate successful separation and wash of the suspended solid (i.e., the precipitate), a tracer, namely Tryptophan, was supplemented to the precipitate suspension. Carry over of fluid parts originally comprised in the precipitate suspension to the wash fluid and thus the collected solids could be monitored via absorbance measurement based on the absorbance maximum at 280 nm of Tryptophan. Samples to be measured were taken after every solid collection cycle from the fluid streams leaving the assembly. The data plotted in FIG. 21 (see also Table 7) show low yield of Tryptophan in the collected solids suspended in the wash solution over the entire range of collection flow rates tested. Low Tryptophan yield in the wash fluid corresponds to low carry over from the solid bearing fluid to be separated. Consequently, the largest fraction of fluid present in the collected solids fraction was wash buffer, which demonstrates efficient precipitate wash.

TABLE 7

Yield values of Tryptophan in the fraction containing the collected solids (i.e. the precipitate) suspended in wash fluid obtained at varying collection flow rates. Tryptophan was originally comprised in the precipitate suspension. The volume of the discharge fraction was 40 mL independent of the discharge volumetric flow rate.

| Number of discharge cycle at volumetric flow rate [—] | Volumetric flow [mL/min] | Yield of amino acid in the wash solution bearing the collected solids [%] |
| --- | --- | --- |
| 1 | 20 | 1.02 |
| 2 | 20 | 2.25 |
| 3 | 20 | 3.91 |
| 4 | 20 | 6.45 |
| 5 | 20 | 6.47 |
| 1 | 40 | 10.14 |
| 2 | 40 | 7.43 |
| 3 | 40 | 5.34 |
| 4 | 40 | 4.65 |
| 5 | 40 | 5.15 |
| 1 | 60 | 5.22 |
| 2 | 60 | 4.30 |
| 3 | 60 | 3.78 |
| 4 | 60 | 4.25 |
| 5 | 60 | 4.07 |

Example 6 for "Bottom Section for being Connected to an Assembly with Plate Settler, and Assembly with Plate Settler" (Separation of a Precipitate at Various Collection Flow Rates in the Presence of a Colorant)

In example 6, a precipitate suspension was separated into its solid fraction, i.e. the precipitate, and its fluid fraction, i.e. the precipitation supernatant. The precipitate suspension was produced by supplementation of an aqueous solution comprising 10 mM Tris(hydroxymethyl)-aminomethan and 100 mM sodium chloride pH 8.5 with 2.7 mM phosphate ions and 15 mM calcium ions. The precipitate suspension was directly and continuously transported to the inlet of the bottom section in assembly with the inclined plate settler. In these examples, the inclined plate settler was inclined at by an angle $\alpha'=30°$ from vertical. The inclined plate settler was made from stainless steel where the surfaces in contact with process fluid were electro polished to Ra<0.6 μm. The internal hold-up volume consisting of bottom section and an inclined plate settler with a single settling channel was 630 mL. A wash solution was supplied to and used with the bottom section. The wash fluid was an aqueous solution containing 2 mM Tris(hydroxymethyl)-aminomethan, 252 mM sodium chloride, 6 mM calcium chloride and 25 mg/L Patent Blue V, which has an absorbance maximum at 620 nm. The wash fluid density must be higher than the density of the fluid in the precipitate suspension and lower than the density of the suspended solids in order for the solids to settle from the fluid they were originally suspended in into the wash buffer provided in the bottom section. For the precipitate suspension and the wash fluid in this example, the densities were matching this criterion.

During operation of the assembly, the solid depleted fluid was continuously collected from the top outlet of the assembly. Separated solids, were collected from the collection channels of the bottom section at regular timely intervals of 15 min. Solid collection was achieved by simultaneous action of the wash fluid and the solid collection pump at volumetric flow rates of 20, 40 and 60 mL/min.

Figure 22:
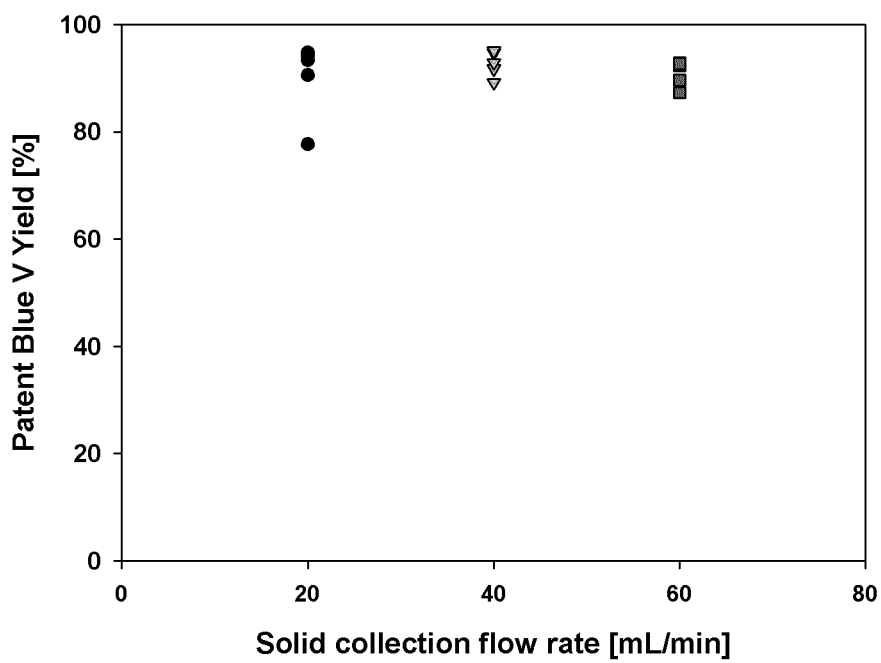
FIG. 22 Yield of Patent Blue V in the fraction containing the collected solids suspended in wash fluid obtained at varying collection flow rates. Patent Blue V was originally comprised in the wash fluid.

In order to demonstrate successful separation and wash of the suspended solid (i.e., the precipitate), a tracer, namely Patent Blue V, was supplemented to the wash fluid. Carry over of fluid parts originally comprised in the precipitate suspension to the wash fluid and thus the collected solids could be monitored via absorbance measurement based on the absorbance maximum at 620 nm of Patent Blue V. Samples for analysis were taken after every solid collection cycle from the fluid streams leaving the assembly. The data plotted in FIG. 22 (see also Table 8) show high yield of Patent Blue V in the collected solids suspended in wash fluid. Here, low yield corresponds to high carry over from the solid bearing fluid to be separated. Therefore, the high yield values support successful separation of precipitate from the precipitate suspension with efficient wash of the collected precipitate.

TABLE 8

Yield values of Patent Blue V collected solids suspended in wash fluid obtained at varying collection flow rates. Patent Blue V was originally comprised in the wash fluid. The volume of the discharge fraction was 40 mL independent of the discharge volumetric flow rate.

| Number of discharge cycle at volumetric flow rate [—] | Volumetric flow [mL/min] | Yield of colorant in the wash solution bearing the collected solids [%] |
| --- | --- | --- |
| 1 | 20 | 77.7 |
| 2 | 20 | 90.6 |
| 3 | 20 | 94.2 |
| 4 | 20 | 93.4 |
| 5 | 20 | 94.8 |
| 1 | 40 | 89.2 |
| 2 | 40 | 91.8 |
| 3 | 40 | 94.7 |
| 4 | 40 | 95.1 |
| 5 | 40 | 92.9 |
| 1 | 60 | 87.3 |
| 2 | 60 | 92.9 |
| 3 | 60 | 92.4 |
| 4 | 60 | 92.7 |
| 5 | 60 | 89.6 |

It will be apparent to those skilled in the art that various modifications and variations can be made in the disclosed devices and systems without departing from the scope of the disclosure. Other aspects of the disclosure will be apparent to those skilled in the art from consideration of the specification and practice of the features disclosed herein. It is intended that the specification and examples be considered as exemplary only. Many additional variations and modifications are possible and are understood to fall within the framework of the disclosure.

The invention claimed is:

1. A bottom section configured to be connected to an assembly for separating a solid component from a fluid, said assembly including an inclined plate settler with at least one sedimentation channel for letting a solid component to be separated settle, said plate settler comprising a lower portion and an upper portion, wherein said at least one sedimentation channel extends from the lower portion to the upper portion, wherein the bottom section is configured to be connected to the lower portion of the inclined plate settler, the bottom section comprising:
    at least one inlet channel configured to feed a fluid comprising the solid component to be separated to the plate settler,
    at least one collection channel configured to collect a settled component descending from the at least one sedimentation channel, and
    at least one wash fluid supply channel for supplying a wash fluid to one sedimentation channel or to one collection channel, said at least one wash fluid supply channel being fluidly separated from other wash fluid supply channels and from all inlet channels,
    wherein said at least one inlet channel and said at least one collection channel are fluidly separated from each other, said inlet channel and said collection channel configured to be connected to said at least one sedimentation channel to form fluid connections between said at least one inlet channel and said at least one sedimentation channel and between said at least one collection channel and said at least one sedimentation channel, respectively.

2. The bottom section of claim 1, connected to an assembly with a plate settler comprising a plurality of sedimentation channels and separation plates separating neighboring sedimentation channels, the bottom section comprising a plurality of inlet channels and a plurality of collection channels, wherein said at least one inlet channel and said at least one collection channel are fluidly separated from all remaining inlet and collection channels, respectively, and
    wherein the flow connection between said at least one inlet channel and the corresponding sedimentation channel and said at least one collection channel and the corresponding sedimentation channel are separate from fluid connections between all other sedimentation channels and all other inlet channels and collection channels, respectively.

3. The bottom section of claim 2, comprising one individual inlet channel and one individual collection channel for at least 50% of the sedimentation channels of a corresponding assembly, to which the bottom section is configured to be connectable, wherein a separate fluid connection is formable for each corresponding pair of inlet channel and sedimentation channel and for each corresponding pair of collection channel and sedimentation channel, respectively.

4. The bottom section of claim 2, comprising one individual collection channel and one individual inlet channel for each of the plurality of sedimentation channels.

5. The bottom section of claim 1, wherein the bottom section is configured to be connected to an assembly oriented in a use position, such that end portions of the inlet channels and end portions of the collection channels proximate to the plate settler extend in the direction of gravity.

6. The bottom section of claim 1, wherein the at least one wash fluid supply channel and the at least one collection channel corresponding to the same sedimentation channel are fluidly connected by an opening in a wall portion shared by said wash fluid supply channel and said collection channel.

7. The bottom section of claim 1 in combination with the plate settler, the bottom section comprising:
    at least one intrachannel distributing portion for evenly distributing a fluid flow through a part of a first channel configured to be proximate to a corresponding sedimentation channel over at least one direction of extension across the cross-section of said particular channel, wherein said first channel is an inlet channel or a collection channel or a wash fluid supply channel; and/or
    at least one interchannel distributing portion for evenly distributing a fluid flow in the direction to or the direction from a plate settler over a plurality of inlet channels and/or wash fluid supply channels and/or collection channels.

8. The bottom section of claim 7, wherein the intrachannel distributing portion and the interchannel distributing portion are connected, the intrachannel distributing portion being configured to be arranged more proximately to the plate settler than the interchannel distributing portion.

9. The bottom section of claim 7, wherein all of the inlet channels and the collection channels are provided in pairs or as triplets together with one wash fluid supply channel each, and wherein all of the inlet channels are fueled by one corresponding interchannel distributing portion each, all of the collection channels are joined by one corresponding interchannel distributing portion; and/or
    wherein all of the inlet channels are associated with one intrachannel distributing portion, and all of the collection channels are associated with one intrachannel distributing portion.

10. The bottom section of claim 9, wherein all wash fluid supply channels are fueled by one corresponding interchannel distributing portion each.

11. The bottom section of claim 9, wherein all of the wash fluid supply channels are associated with one intrachannel distributing portion.

12. The bottom section collection of claim 7, comprising intrachannel distributing portions and interchannel distributing portions, wherein the distributing direction of the interchannel distributing portions is perpendicular to the distributing direction of the intrachannel distributing portions.

13. The bottom section collection of claim 12, wherein the distributing direction of the intrachannel distributing portions is a longitudinal extension direction of a cross-section of a connecting end part of the first channel to be located proximate to the plate settler.

14. The bottom section according to claim 1 in combination with the plate settler having the at least one sedimentation channel, wherein bottom surfaces of neighboring sedimentation channels extend parallel to one another and include at least a part that is not inclined in any direction other than the direction of inclination of the sedimentation channels, and/or
    wherein the angle of inclination of the sedimentation channels with respect to the direction of gravity lies in a range of 15° to 85°.

15. A method for separating solid components from a fluid, wherein the method comprises the following steps (i) to (iv):

(i) feeding fluid comprising the solid components to the at least one inlet channel of the bottom section of any one of claims 1 and 6 to 14;
(ii) letting the solid components settle;
(iii) draining the rest fluid;
(iv) collecting the settled components through the at least one collection channel of said bottom section.

16. The method for separating solid components from a fluid according to claim 15, wherein the solid components to be separated are precipitates.

17. The method for separating solid components from a fluid according to claim 15, wherein the solid components to be separated are cells.

18. The method for separating solid components from a fluid according to claim 17, wherein the cells are capable of producing a biologically active substance and wherein the fluid contains said biologically active substance.

19. The method for separating solid components from a fluid according to claim 18, wherein the biologically active substance is a coagulation factor, or wherein the biologically active substance is Factor VIII.

20. The method for separating solid components from a fluid according to claim 15, wherein the bottom section is comprised in said assembly, and wherein the step of letting the solid components settle is a step of letting the solid components settle in the at least one sedimentation channel of the inclined plate settler.

21. The method for separating solid components from a fluid according to claim 20, wherein in step (iii) the rest fluid is drained at the upper portion of the at least one sedimentation channel.

22. The method for separating solid components from a fluid according to claim 21, wherein the amount of solid components in the drained rest fluid is less than 20% of the amount of solid components in the fluid that is fed to the at least one inlet channel of the bottom section.

23. The method for separating solid components from a fluid according to claim 21, wherein the solid components to be separated are cells, wherein the cells are capable of producing a biologically active substance, wherein the fluid contains said biologically active substance, and wherein the amount of biologically active substance in the drained rest fluid is more than 80% of the amount of biologically active substance in the fluid that is fed to the at least one inlet channel of the bottom section.

24. The method for separating solid components from a fluid according to claim 15, wherein the fluid comprising the solid components is continuously fed to the at least one inlet channel of the bottom section.

25. The method for separating solid components from a fluid according to claim 15, wherein the method is performed at a temperature of between 0° C. and 10° C. or at a temperature of between 2° C. and 8° C.

26. An assembly for separating a solid component from a fluid, the assembly comprising an inclined plate settler with a lower portion, an upper portion, and at least one sedimentation channel for letting a solid component to be separated settle, said sedimentation channel extend from the lower portion to the upper portion,
the plate settler being configured to be oriented during use such that the at least one sedimentation channel extends from the lower portion to the upper portion in a direction that is inclined with respect to the direction of gravity,
wherein the at least one sedimentation channel is connected to a fluid outlet for draining a rest fluid at the upper portion and connected to a bottom section according to claim 1 at the lower portion.

27. The assembly according to claim 26, comprising a plurality of sedimentation channels for letting a solid component to be separated settle, said sedimentation channels extending from the lower portion to the upper portion, and the plate settler further comprising separation plates separating neighboring channels,
wherein the plurality of sedimentation channels is connected to at least one fluid outlet for draining a rest fluid at the upper portion and connected to the bottom section at the lower portion.

28. The assembly according to claim 26, wherein a relative difference between hydrostatic pressures in different sedimentation channels does not exceed a threshold of 10%.

29. The assembly according to claim 28, wherein a relative difference between hydrostatic pressures in different sedimentation channels does not exceed a threshold of 3%.

30. The assembly according to claim 26, further comprising a fluid comprising a solid component to be separated to the plate settler through the at least one inlet channel, and a wash buffer fluid through the at least one wash fluid supply channel,
wherein a density of the wash buffer fluid is equal to or higher than a density of the fluid comprising the solid component to be separated.

31. A bottom section configured to be connected to an assembly for separating a solid component from a fluid, said assembly including an inclined plate settler with at least one sedimentation channel for letting a solid component to be separated settle, said plate settler comprising a lower portion and an upper portion, wherein said at least one sedimentation channel extends from the lower portion to the upper portion, wherein the bottom section is configured to be connected to the lower portion of the inclined plate settler, the bottom section comprising:
at least one inlet channel configured to feed a fluid comprising the solid component to be separated to the plate settler,
at least one collection channel configured to collect a settled component descending from the at least one sedimentation channel,
at least one intrachannel distributing portion for evenly distributing a fluid flow through a part of a first channel proximate to a corresponding sedimentation channel over at least one direction of extension across the cross-section of said particular channel,
wherein said at least one inlet channel and said at least one collection channel are fluidly separated from each other, said inlet channel and said collection channel configured to be connected to said at least one sedimentation channel to form fluid connections between said at least one inlet channel and said at least one sedimentation channel and between said at least one collection channel and said at least one sedimentation channel, respectively,
wherein said first channel is an inlet channel or a collection channel or a wash fluid supply channel,
wherein an upper part of the first channel is located proximate to the corresponding sedimentation channel,
wherein a lower part of the first channel is split into two connecting channels of equal first cross-sections, and said connecting channels are at least once further split into respective connecting sub-channels of respective other equal cross-sections, wherein the first cross-sections are identical to or different from the respective other cross-sections, and wherein end portions of all of the connecting sub-channels after the respective last splits are connected to the upper part so as to be evenly distributed over a distributing direction.

32. A bottom section configured to be connected to an assembly for separating a solid component from a fluid, said assembly including an inclined plate settler with at least one sedimentation channel for letting a solid component to be separated settle, said plate settler comprising a lower portion and an upper portion, wherein said at least one sedimentation channel extends from the lower portion to the upper portion, wherein the bottom section is configured to be connected to the lower portion of the inclined plate settler, the bottom section comprising:
at least one inlet channel configured to feed a fluid comprising the solid component to be separated to the plate settler,
at least one collection channel configured to collect a settled component descending from the at least one sedimentation channel,
at least one interchannel distributing portion for evenly distributing a fluid flow in the direction to or the direction from a plate settler over a plurality of inlet channels and/or wash fluid supply channels and/or collection channels,
wherein said at least one inlet channel and said at least one collection channel are fluidly separated from each other, said inlet channel and said collection channel configured to be connected to said at least one sedimentation channel to form fluid connections between said at least one inlet channel and said at least one sedimentation channel and between said at least one collection channel and said at least one sedimentation channel, respectively,
wherein the interchannel distributing portion comprises an upper portion to be connected to one or several inlet channels or one or several wash fluid channels or one or several collection channels, and a lower portion, and
wherein the lower part is split into two connection channels of equal first cross-section.

33. The bottom section of claim 32, wherein said connection channels are at least once further split into respective connection sub-channels of respective other equal cross-sections, wherein the first cross-sections are identical to or different from the respective other cross-sections, and wherein end portions of all of the connection sub-channels after the respective last splits are connected to the upper portion so as to be evenly distributed over a distributing direction.

34. A bottom section configured to be connected to an assembly for separating a solid component from a fluid, said assembly including an inclined plate settler with at least one sedimentation channel for letting a solid component to be separated settle, said plate settler comprising a lower portion and an upper portion, wherein said at least one sedimentation channel extends from the lower portion to the upper portion, wherein the bottom section is configured to be connected to the lower portion of the inclined plate settler, the bottom section comprising:
at least one inlet channel configured to feed a fluid comprising the solid component to be separated to the plate settler,
at least one collection channel configured to collect a settled component descending from the at least one sedimentation channel,
at least one intrachannel distributing portion for evenly distributing a fluid flow through a part of a first channel proximate to a corresponding sedimentation channel over at least one direction of extension across the cross-section of said particular channel,
wherein said at least one inlet channel and said at least one collection channel are fluidly separated from each other, said inlet channel and said collection channel configured to be connected to said at least one sedimentation channel to form fluid connections between said at least one inlet channel and said at least one sedimentation channel and between said at least one collection channel and said at least one sedimentation channel, respectively,
wherein said first channel is an inlet channel or a collection channel or a wash fluid supply channel,
wherein the intrachannel distributing portion includes a fractal flow distributor.

35. A bottom section configured to be connected to an assembly for separating a solid component from a fluid, said assembly including an inclined plate settler with at least one sedimentation channel for letting a solid component to be separated settle, said plate settler comprising a lower portion and an upper portion, wherein said at least one sedimentation channel extends from the lower portion to the upper portion, wherein the bottom section is configured to be connected to the lower portion of the inclined plate settler, the bottom section comprising:
at least one inlet channel configured to feed a fluid comprising the solid component to be separated to the plate settler,
at least one collection channel configured to collect a settled component descending from the at least one sedimentation channel,
at least one interchannel distributing portion for evenly distributing a fluid flow in the direction to or the direction from a plate settler over a plurality of inlet channels and/or wash fluid supply channels and/or collection channels,
wherein said at least one inlet channel and said at least one collection channel are fluidly separated from each other, said inlet channel and said collection channel configured to be connected to said at least one sedimentation channel to form fluid connections between said at least one inlet channel and said at least one sedimentation channel and between said at least one collection channel and said at least one sedimentation channel, respectively,
wherein the interchannel distributing portion includes a fractal flow distributor.

36. A bottom section for being connected to an assembly for separating a solid component from a fluid, said assembly including an inclined plate settler with at least one sedimentation channel for letting a solid component to be separated settle, said plate settler comprising a lower portion and an upper portion, wherein said at least one sedimentation channel extends from the lower portion to the upper portion, wherein the bottom section is configured to be connected to the lower portion of the inclined plate settler, the bottom section comprising:
at least one inlet channel for feeding a fluid comprising the solid component to be separated to the plate settler, and
at least one collection channel for collecting a settled component descending from the at least one sedimentation channel,
wherein said at least one inlet channel and said at least one collection channel are fluidly separated from each other, said inlet channel and said collection channel being connectable to said at least one sedimentation channel, to form fluid connections between said at least one inlet channel and said at least one sedimentation channel and between said at least one collection channel and said at least one sedimentation channel, respectively, and wherein the bottom section is configured to be connected to an assembly oriented in a use position, such that end portions of the inlet channels and end portions of the collection channels proximate to the plate settler extend vertically.

* * * * *